(12) United States Patent
Noyori et al.

(10) Patent No.: US 8,212,037 B2
(45) Date of Patent: Jul. 3, 2012

(54) PROCESS FOR PRODUCTION OF OPTICALLY ACTIVE QUINUCLIDINOLS

(75) Inventors: Ryoji Noyori, Aichi (JP); Takeshi Okuma, Hokkaido (JP); Kunihiko Tsutsumi, Saitama (JP); Noriyuki Utsumi, Saitama (JP); Kunihiko Murata, Saitama (JP); Takeaki Katayama, Saitama (JP)

(73) Assignees: Kanto Kagaku Kabushiki Kaisha, Tokyo (JP); Nagoya Industrial Science Research Institute, Nagoya-Shi, Aichi (JP)

(*) Notice: Subject to any disclaimer, the term of this patent is extended or adjusted under 35 U.S.C. 154(b) by 702 days.

(21) Appl. No.: 11/887,340

(22) PCT Filed: Mar. 30, 2005

(86) PCT No.: PCT/JP2005/006048
§ 371 (c)(1),
(2), (4) Date: Mar. 3, 2009

(87) PCT Pub. No.: WO2006/103756
PCT Pub. Date: Oct. 5, 2006

(65) Prior Publication Data
US 2009/0216019 A1    Aug. 27, 2009

(51) Int. Cl.
*C07F 15/00* (2006.01)
*C07D 453/02* (2006.01)

(52) U.S. Cl. .............................. 546/2; 546/137; 548/402
(58) Field of Classification Search .............. 546/2, 137; 548/402
See application file for complete search history.

(56) References Cited

U.S. PATENT DOCUMENTS

| 5,744,606 | A  | 4/1998 | Brieden |
| 6,790,973 | B2 | 9/2004 | Tsutsumi et al. |

FOREIGN PATENT DOCUMENTS

| JP | 09-194480 | 7/1997 |
| JP | 2003-252884 | 9/2003 |
| JP | 2003-277380 | 10/2003 |
| JP | 2007-536338 A | 12/2007 |
| WO | WO 2005/105819 A1 | 11/2005 |

OTHER PUBLICATIONS

Baratta, Walter et al., "2-(Aminomethyl)pyridine-Phosophine Ruthenium(II) Complexes: Novel Highly Active Transfer Hydrogenation Catalysts," *Organometallics* 2005; 24(7):1660-1669.

*Primary Examiner* — Charanjit Aulakh
(74) *Attorney, Agent, or Firm* — Wolf, Greenfield & Sacks, P.C.

(57) ABSTRACT

A novel ruthenium complex which is a highly efficient catalyst useful for the production of optically active 3-quinuclidinols, and a process for production of optically active 3-quinuclidinols using the ruthenium complex as a catalyst, where the optically active 3-quinuclidinols are useful as an optically active, physiologically active compound utilized in medicines and agrichemicals or as a synthetic intermediate such as a liquid crystal material.

9 Claims, No Drawings

US 8,212,037 B2

PROCESS FOR PRODUCTION OF OPTICALLY ACTIVE QUINUCLIDINOLS

RELATED APPLICATIONS

This application is a national stage filing under 35 U.S.C. §371 of PCT International application PCT/JP2005/006048, filed Mar. 30, 2005.

TECHNICAL FIELD

The present invention relates to a novel ruthenium complex, and to a process for preparing optically active 3-quinuclidinols using said complex as a catalyst. More particularly, the invention relates to a novel ruthenium complex, which is a highly efficient catalyst useful for preparing optically active 3-quinuclidinols effective as synthetic intermediates for optically active and physiologically-active compounds utilized in pharmaceuticals and agricultural chemicals or for liquid-crystal materials, and to a process for preparing optically active 3-quinuclidinols using this ruthenium complex as a catalyst.

BACKGROUND ART

There are many optically active organic compounds which occur naturally. In many of these compounds with a physiologically active type, only one kind of enantiomer has a desired activity. The other kind of enantiomer without the desired activity does not have a physiological activity useful in organisms, and in addition, in some cases it is known to be rather toxic to organisms. Therefore, as a safe synthetic method of pharmaceuticals, the development of a process for synthesizing desired compounds, or optically active compounds with high optical purity which are used as their intermediates, has been desired.

Optically active alcohols are useful as asymmetric sources for the synthesis of various optically active materials. They are generally prepared by optical resolution of racemates, or by asymmetric synthesis which uses biological catalysts or asymmetric metal complexes as a catalyst. In particular, the preparation of optically active alcohols by asymmetric synthesis is considered to be an indispensable technology for the preparation of a large amount of optically active alcohols. (R)-3-quinuclidinol is one of the industrially useful optically active alcohols as a synthetic intermediate for optically active and physiologically-active compounds utilized in pharmaceuticals and agricultural chemicals or for liquid crystal materials. optically active 3-quinuclidinol is used as an important intermediate for various physiologically-active or pharmacologically-active ingredients in, for example, therapeutic agents for arteriosclerosis having a squalene-synthase inhibitory effect, bronchodilators having a muscarine-receptor antagonistic activity, and inhibitors of gastrointestinal motility. As a conventional process for the preparation of optically active 3-quinuclidinol, for example, a process by the resolution of an acetylated form of racemic 3-quinuclidinol using optically active tartaric acid followed by hydrolysis is known. However, to increase optical purity, complex operations including repetition of re-crystallization for more than several times are required. In addition, as a process to utilize microorganisms and enzymes, the following process is known: a substance such as racemic 3-quinuclidinol ester is used as a raw material, to which the microorganisms and enzymes listed below are reacted for the selective and asymmetric hydrolysis of (S)-3-quinuclidinol ester, so that the remaining (R)-3-quinuclidinol ester is hydrolyzed to obtain (R)-3-quinuclidinol; as microorganisms and enzymes, for example, subtilisin protease, *Aspergillus*- or *Pseudomonas*-derived esterolytic enzyme, or microorganisms and enzymes belonging to *Aspergillus, Rhizopus, Candida* or *Pseudomonas* are used. Also reported is a process wherein racemic 3-quinuclidinol ester is used as a raw material, and (R)-3-quinuclidinol ester is selectively asymmetric-hydrolized using mare serum esterase. Furthermore, a process using racemic 3-quinuclidinol as a raw material, wherein only (S) form are converted to (S)-3-quinuclidinyl butyric acid using subtilisin protease, so that (R) forms are prepared, is known. However, these processes have problems such as low optical purity or difficulty in mass production due to complex synthetic processes. Moreover, because any of these processes is a method to obtain a desired optical enantiomer by optical resolution of racemic 3-quinuclidinol, the other undesired enantiomer remains. Accordingly in these processes, additional processes are required for undesired enantiomers, such as a process to reverse the steric configuration of asymmetric carbons in an undesired enantiomer to convert it into the desired one, or a process to convert an undesired enantiomer into a racemate and to obtain the desired one by re-application of optical resolution; as a result, production cost increases. Thus, any of these processes is far from a simple, economically efficient and effective process for the preparation of (R)-3-quinuclidinol. Other known processes include a process for preparing optically active 3-quinuclidinol from 3-quinuclidinone utilizing asymmetric reductive reaction by microorganisms and enzymes. In these reactions, wild-type microorganisms are reacted to substrate compounds to directly produce optically active compounds. This reaction process is a one-step reaction, achieving significant simplification of the reaction process. However, problems such as low optical purity and low accumulation concentration of products still exist.

As a process to obtain optically active alcohol, there is a process for the asymmetric hydrogenation of prochiral carbonyl compounds in the presence of an asymmetric metal complex catalyst. As an example, a process for the asymmetric hydrogenation of carbonyl compounds in the presence of a ruthenium metal complex having an optically active diphosphine compound such as BINAP, etc. as the ligand, a base such as a hydroxide of alkali metal or alkaline earth metal, and an optically active 1,2-ethylenediamine-type diamine compound, is disclosed. In addition, a process for the hydrogenation of carbonyl compounds using a ruthenium complex having an optically active diphosphine compound such as BINAP, etc. and an optically active 1,2-ethylenediamine-type diamine compound as the ligands, is disclosed. Furthermore, it is reported in JP A No. 2003-252884 that when a ruthenium complex having an optically active phosphine compound such as SKEWPOHS, etc. and an optically active 1,2-ethylenediamine-type diamine compound as the ligands is used, various carbonyl compounds can be effectively hydrogenated; however, there is no mentioning of the application of this method to quinuclidinones.

As a synthetic method of optically active 3-quinuclidinol, JP A No. 9-194480 discloses a method for hydrogenating a quinuclidinone derivative selected from the compounds consisting of 3-quinuclidinone and its adduct with Lewis acid, and specific tertiary and quaternary salts corresponding therewith, in the presence of a rhodium, iridium or ruthenium complex having an optically active diphosphine compound as the ligand. However, when 3-quinuclidinone was asymmetrically hydrogenated, the enantiometric excess of the optically active 3-quinuclidinol obtained was extremely low at 20% or less. The enantiometric excess improved when tertiary and quaternary salts of 3-quinuclidinone were used, but complex processes for the conversion into tertiary and quaternary salts, and for the conversion into 3-quinuclidinol educts after hydrogenation were required. JP A No. 2003-277380 discloses a process for the preparation of optically active 3-quinucleidinol by hydrogenating 3-quinuclidinone, in the presence of an optically active ruthenium complex having an optically active bidentate diphosphine compound and an optically active 1,2-ethylenediamine-type diamine compound as the ligands, and a base. Another process to hydrogenate carbonyl compounds containing 3-quinuclidinone using a rhodium complex as a catalyst, wherein said complex has an optically active phosphine compound with ferrocene backbone and an optically active 1,2-ethylenediamine-type diamine compound, is also disclosed. However, these processes were not industrially satisfactory due to their low activity and low optical purity.

DISCLOSURE OF THE INVENTION

Problem to be Solved by the Invention

Under these circumstances, the purpose of the present invention is to provide a novel ruthenium complex having an optically active diphosphine compound with asymmetry on carbon which is easily synthesized and a specific diamine compound or an optically active diamine compound as the ligands, and to provide a process for preparing an optically active alcoholic compound using said complex as a catalyst, that is a process for preparing an optically active 3-quinuclidinols which is superior than a process with conventional ruthenium complex having an optically active diphosphine compound with axial asymmetry and an optically active 1,2-ethylenediamine-type diamine compound as the ligands, in terms of reactivity and enantioselectivity in the asymmetric hydrogenation reaction of 3-quinuclidinones.

The inventors of the present invention devoted themselves to studies to achieve the above purpose. As an optically active diphosphine compound having asymmetry on carbon, there is, for example, an optically active SKEWPHOS. The inventors noticed that said compound can easily be synthesized without optical resolution using an optically active 2,4-pentanediol obtained from 2,4-pentanedione as a raw material, so they synthesized a variety of novel ruthenium complexes having an optically active SKEWPHOS derivative and a specific diamine compound or an optically active diamine compound as the ligands, and made extensive studies on their performance as an asymmetric hydrogenation catalyst for 3-quinuclidinones. As a result, the inventors found that a novel ruthenium complex catalyst having an optically active SKEWPHOS derivative compound and a specific diamine compound or an optically active diamine compound as the ligands has excellent properties as an asymmetric hydrogenation catalyst for 3-quinuclidinones, and that the above purpose can be achieved, thus accomplishing the invention.

Means of Solving the Problem

Namely, the invention relates to a ruthenium complex of general formula (1):

RuXYAB (1)

wherein X and Y may be mutually identical or different and denote hydrogen or an anion group, A is a compound of general formula (2):

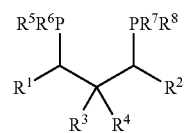

(2)

(wherein $R^1$ and $R^2$ may be mutually identical or different and are an alkyl group having a carbon number of 1-20 or a cyclic hydrocarbon group which may have one or more substituents; $R^3$ and $R^4$ may be mutually identical or different and are hydrogen or a hydrocarbon group having a carbon number of 1-3; $R^5$, $R^6$, $R^7$ and $R^8$ may be mutually identical or different and are a hydrocarbon group which may have one or more substituents), B is a compound of general formula (3) or (4):

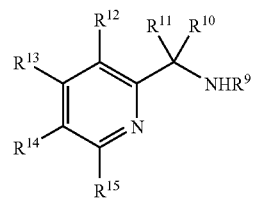

(3)

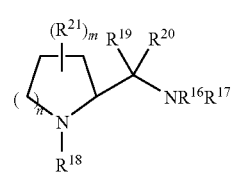

(4)

(wherein in general formula (3), $R^9$ denotes a hydrogen atom, an alkyl group having a carbon number of 1-20 or a cyclic hydrocarbon group which may have one or more substituents; $R^{10}$ and $R^{11}$ may be mutually identical or different and denote a hydrogen atom, an alkyl group having a carbon number of 1-20 or a cyclic hydrocarbon group which may have one or more substituents, $R^{10}$ and $R^{11}$ may be mutually bonded to form a saturated or unsaturated hydrocarbon group which may have one or more substituents of alkyl, alkenyl, cycloalkyl, aryl, alkoxy, ester, acyloxy, halogen atoms, nitro, or cyano; $R^{12}$, $R^{13}$, $R^{14}$ and $R^{15}$ may be mutually identical or different and denote a hydrogen atom, an alkyl group having a carbon number of 1-20 or a cyclic hydrocarbon group which may have one or more substituents, $R^{12}$ and $R^{13}$, $R^{13}$ and $R^{14}$, or $R^{14}$ and $R^{15}$ may be mutually bonded to form a saturated or unsaturated hydrocarbon group, or to form a saturated or unsaturated hydrocarbon group containing N; wherein in general formula (4), at least one of $R^{16}$, $R^{17}$ and $R^{18}$ is a hydrogen atom, $R^{16}$ and $R^{17}$ may be mutually identical or different and denote a hydrogen atom, an alkyl group having a carbon number of 1-20 or a cyclic hydrocarbon group which may have one or more substituents, or $R^{16}$ and $R^{17}$ may be mutually bonded to form a ring containing N, $R^{18}$ denotes a hydrogen atom, an alkyl group having a carbon number of 1-20 or a cyclic hydrocarbon group which may have one or more substituents; $R^{19}$ and $R^{20}$ may be mutually identical or different and denote a hydrogen atom, an alkyl group having a carbon number of 1-20 or a cyclic hydrocarbon group which may have one or more substituents, $R^{19}$ and $R^{20}$ may be mutually bonded to form a saturated or unsaturated hydrocarbon group which may have one or more substituents of alkyl, alkenyl, cycloalkyl, aryl, alkoxy, ester, acyloxy, halogen atoms, nitro, or cyano; $R^{21}$ may be mutually identical or different and independently denote a hydrogen atom, an alkyl group having a carbon number of 1-20 or a cyclic hydrocarbon group which may have one or more substituents, and adjacent $R^{21}$ may be mutually bonded to form a saturated or unsaturated hydrocarbon group; m denotes an integer of 1-10; n denotes an integer of 1-3), and wherein the ruthenium may be arbitrarily coordinated with each ligand.

In addition, the invention relates to the above ruthenium complex, wherein

A is one selected from the group consisting of SKEWPHOS: 2,4-bis(diphenylphosphino)pentane, TolSKEWPHOS:2,4-bis(di-4-tolylphosphino)pentane, XylSKEWPHOS:2,4-bis(di-3,5-xylylphosphino)pentane, 4-t-BuSKEWPHOS: 2,4-bis[di(4-t-butylphenyl)phosphino]pentane, 3,5-diEtSKEWPHOS:2,4-bis[bis(3,5-diethylphenyl) phosphino]pentane, 2,4-bis(diphenylphosphino)-3-methylpentane, 2,4-bis(di-4-tolylphosphino)-3-methylpentane, 2,4-bis(di-3,5-xylylphosphino)-3-methylpentane, 2,4-bis[di(4-t-butylphenyl)phosphino]-3-methylpentane, 2,4-bis[bis(3,5-diethylphenyl) phosphino]-3-methylpentane, 1,3-bis (diphenylphosphino)-1,3-diphenylpropane, 1,3-bis(di-4-tolylphosphino)-1,3-diphenylpropane, 1,3-bis(di-3,5-xylylphosphino)-1,3-diphenylpropane, 1,3-bis[di(4-t-butylphenyl)phosphino]-1,3-diphenylpropane, 1,3-bis[bis (3,5-diethylphenyl)phosphino]-1,3-diphenylpropane, 1,3-bis(diphenylphosphino)-1,3-diphenyl-2-methylpropane, 1,3-bis(di-4-tolylphosphino)-1,3-diphenyl-2-methylpropane, 1,3-bis(di-3,5-xylylphosphino)-1,3-diphenyl-2-methylpropane, 1,3-bis[di(4-t-butylphenyl)phosphino]-1,3-diphenyl-2-methylpropane, and 1,3-bis[bis(3,5-diethylphenyl)phosphino]-1,3-diphenyl-2-methylpropane, B is one represented by general formula (3), wherein $R^9$ denotes a hydrogen atom, an alkyl group having a carbon number of 1-10 or a cyclic hydrocarbon group which may have one or more substituents; $R^{10}$ and $R^{11}$ may be mutually identical or different and denote a hydrogen atom, an alkyl group having a carbon number of 1-10 or a cyclic hydrocarbon group which may have one or more substituents, $R^{10}$ and $R^{11}$ may be mutually bonded to form a saturated or unsaturated hydrocarbon group which may have one or more substituents of alkyl, alkenyl, cycloalkyl, aryl, alkoxy, ester, acyloxy, halogen atoms, nitro, or cyano; $R^{12}$, $R^{13}$, $R^{14}$ and $R^{15}$ may be mutually identical or different and denote a hydrogen atom, an alkyl group having a carbon number of 1-10 or a cyclic hydrocarbon group which may have one or more substituents, $R^{12}$ and $R^{13}$, $R^{13}$ and $R^{14}$, or $R^{14}$ and $R^{15}$ may be mutually bonded to form a saturated or unsaturated hydrocarbon group; or by general formula (4), wherein at least one of $R^{16}$, $R^{17}$ and $R^{18}$ is a hydrogen atom, $R^{16}$ and $R^{17}$ may be mutually identical or different and denote a hydrogen atom, an alkyl group having a carbon number of 1-10 or a cyclic hydrocarbon group which may have one or more substituents, or $R^{16}$ and $R^{17}$ may be mutually bonded to form a ring containing N, $R^{18}$ denotes a hydrogen atom, an alkyl group having a carbon number of 1-10 or a cyclic hydrocarbon group which may have one or more substituents; $R^{19}$ and $R^{20}$ may be mutually identical or different and denote a hydrogen atom, an alkyl group having a carbon number of 1-10 or a cyclic hydrocarbon group which may have one or more substituents, $R^{19}$ and $R^{20}$ may be mutually bonded to form a saturated or unsaturated hydrocarbon group which may have one or more substituents of alkyl, alkenyl, cycloalkyl, aryl, alkoxy, ester, acyloxy, halogen atoms, nitro, or cyano; $R^{21}$ may be mutually identical or different and denotes a hydrogen atom, an alkyl group having a carbon number of 1-10 or a cyclic hydrocarbon group which may have one or more substituents, and adjacent $R^{21}$ may be mutually bonded to form a saturated or unsaturated hydrocarbon group;

m denotes an integer of 1-10, n denotes an integer of 1-3, and each ligand of the ruthenium may be arbitrarily coordinated.

Furthermore, the invention relates to the above ruthenium complex, wherein

A is one selected from the group consisting of SKEWPHOS: 2,4-bis(diphenylphosphino)pentane, TolSKEWPHOS:2,4-bis(di-4-tolylphosphino)pentane, XylSKEWPHOS:2,4-bis(di-3,5-xylylphosphino)pentane, 4-t-BuSKEWPHOS: 2,4-bis[di(4-t-butylphenyl)phosphino]pentane, and 3,5-diEtSKEWPHOS: 2,4-bis[bis(3,5-diethylphenyl)phosphino]pentane, B is 2-picolylamine or 2-aminomethylpyrrolidine.

In addition, the invention relates to a process for preparing the compound of the above-described general formula (1):

RuXYAB (1)

wherein a compound of general formula (5):

RuXYA (5)

(wherein X, Y and A are as defined in [0006]) is reacted with the compound B to obtain said compound of general formula (1).

Furthermore, the invention relates to a process for preparing an optically active 3-quinuclidinols, wherein a 3-quinuclidinones is reacted with hydrogen or a hydrogen-donating compound in the presence of a ruthenium complex of general formula (1):

RuXYAB (1)

(wherein X is hydrogen, Y is a tetrahydroborate anion or a tetrafluoroborate anion, A and B are as defined in [0006]) to obtain the optically active 3-quinuclidinols.

In addition, the invention relates to a process for preparing an optically active 3-quinuclidinols, wherein a 3-quinuclidinones is reacted with hydrogen or a hydrogen-donating compound in the presence of a ruthenium complex of general formula (1):

RuXYAB (1)

(wherein X, Y, A and B are as defined in [0006]) and a base represented by an alkali metal or alkaline earth metal salt, or a quaternary ammonium salt, to obtain the optically active 3-quinuclidinols.

Furthermore, the invention relates to a process for preparing an optically active 3-quinuclidinols, wherein a 3-quinuclidinones is reacted with hydrogen or a hydrogen-donating compound in the presence of a ruthenium complex of general formula (5):

RuXYA (5)

(wherein X is hydrogen, Y is a tetrahydroborate anion or a tetrafluoroborate anion, and A is as defined in [0006]) and a diamine compound or an optically active diamine compound of general formula (3) or (4):

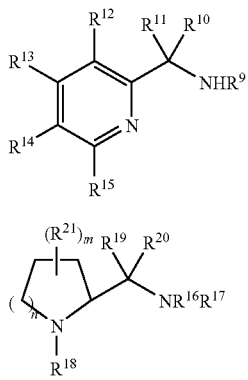
(3)

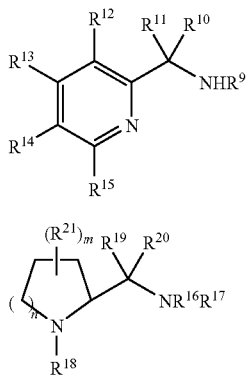
(4)

(wherein $R^9$-$R^{21}$, n and m are as defined in [0006]) to obtain the optically active 3-quinuclidinols.

In addition, the invention relates to a process for preparing an optically active 3-quinuclidinols, wherein a 3-quinuclidinones is reacted with hydrogen or a hydrogen-donating compound in the presence of a ruthenium complex of general formula (5):

$$RuXYA \quad (5)$$

(wherein X, Y and A are as defined in [0006]), a diamine compound or an optically active diamine compound of general formula (3) or (4):

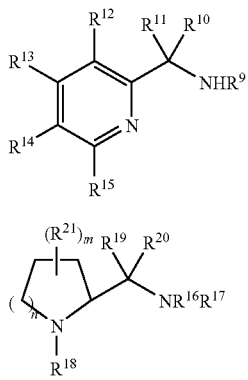
(3)

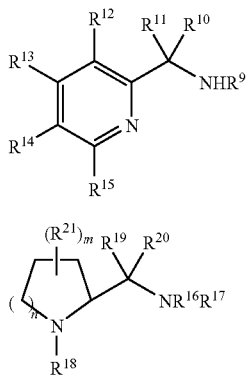
(4)

(wherein $R^9$-$R^{21}$, n and m are as defined in [0006]), and a base such as an alkali metal or alkaline earth metal salt, or a quaternary ammonium salt of, to obtain the optically active 3-quinuclidinols.

Effects of the Invention

The novel ruthenium complex catalyst of the invention, which has an easily synthesized optically active diphosphine compound and a specific diamine compound or an optically active diamine compound as the ligands, can be easily prepared, and moreover, it can reduce 3-quinuclidinones to 3-quinuclidinols with a high yield and high steric selectivity; in addition, it has extremely excellent properties in terms of economic efficiency and production cost.

BEST MODE FOR CARRYING OUT THE INVENTION

The present invention has the characteristics as described above; the mode for carrying out the invention is explained in detail.

First, general formula (1):

$$RuXYAB \quad (1)$$

representing a ruthenium complex of the invention comprises an optically active diphosphine compound A represented by general formula (2):

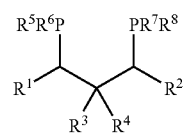
(2)

and a diamine compound or an optically active diamine compound B represented by general formula (3) or (4):

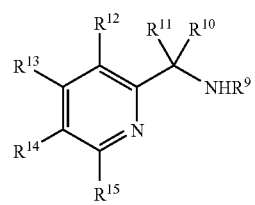
(3)

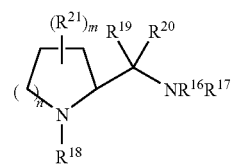
(4)

here, substituents X and Y may be mutually identical or different, and denote a hydrogen atom or an anion group. Said anion group includes, for example, fluorine anion, chlorine anion, bromine anion, iodine anion, acetoxy anion, benzoyloxy anion, (2,6-dihydroxybenzoyl)oxy anion, (2,5-dihydroxybenzoyl)oxy anion, (3-aminobenzoyl)oxy anion, (2,6-methoxybenzoyl)oxy anion, (2,4,6-triisopropylbenzoyl)oxy anion, 1-naphthalenecarboxylic acid anion, 2-naphthalenecarboxylic acid anion, trifluoroacetoxy anion, trifluoromethanesulfoxy anion, tetrahydroborate anion, and tetrafluoroborate anion. Of these, halogen anions such as fluorine anion, chlorine anion, bromine anion and iodine anion, and tetrahydroborate anion and tetrafluoroborate anion are preferred.

The optically active diphosphine compound A in the optically active ruthenium complex of general formula (1) is represented by general formula (2).

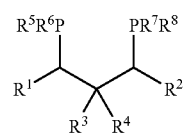
(2)

Here, $R^1$ and $R^2$ may be mutually identical or different and denote an alkyl group having a carbon number of 1-20 or a cyclic hydrocarbon group which may have one or more substituents; $R^3$ and $R^4$ may be mutually identical or different and are hydrogen or a hydrocarbon group having a carbon number of 1-3; $R^5$, $R^6$, $R^7$ and $R^8$ may be mutually identical or different and denote a hydrocarbon group which may have one or more substituents.

Here, $R^1$ and $R^2$ representing an alkyl group or a cyclic hydrocarbon group which may have one or more substituents, may be a saturated or unsaturated, aliphatic or alicyclic hydrocarbon group, a monocyclic or polycyclic, aromatic or araliphatic hydrocarbon group, or any species of these hydrocarbon groups having one or more substituents. Examples include hydrocarbon groups such as alkyl, alkenyl, cycloalkyl, cycloalkenyl, phenyl, naphthyl and phenylalkyl, and said hydrocarbon groups further having various acceptable substituents such as alkyl, alkenyl, cycloalkyl, aryl, alkoxy, ester, acyloxy, halogen atoms, nitro group and cyano group. Among them, methyl, ethyl, propyl and substituted phenyl groups are preferred, and methyl and phenyl groups are particularly preferred.

$R^3$ and $R^4$ representing a hydrocarbon group having a carbon number of 1-3 are an aliphatic saturated hydrocarbon group. Specifically, methyl, ethyl, propyl and isopropyl groups are preferred.

Here, $R^5$, $R^6$, $R^7$ and $R^8$ which may be mutually identical or different, representing a hydrocarbon group which may have a hydrogen atom or one or more substituents, may be a saturated or unsaturated, aliphatic or alicyclic hydrocarbon group, a monocyclic or polycyclic, aromatic or araliphatic hydrocarbon group, or any species of these hydrocarbon groups having one or more substituents. Examples include hydrocarbon groups such as alkyl, alkenyl, cycloalkyl, cycloalkenyl, phenyl, naphthyl and phenylalkyl, and said hydrocarbon groups further having various acceptable substituents such as alkyl, alkenyl, cycloalkyl, aryl, alkoxy, ester, acyloxy, halogen atoms, nitro group and cyano group. Among them, phenyl and substituted phenyl groups are preferred; a phenyl group and a substituted phenyl group with 1 to 5 methyl, ethyl, propyl or t-butyl groups are particularly preferred.

Examples of the optically active diphosphine compound of general formula (2) include the followings:

(1) Illustrative of pentane derivatives having diphenylphosphino groups at 2- and 4-positions are SKEWPHOS having one or two alkyl substituents with a carbon number of 1-3 at 3-position or having no alkyl substituent: 2,4-bis(diphenylphosphino)pentane, 2,4-bis(diphenylphosphino)-3-methylpentane, 2,4-bis(diphenylphosphino)-3,3-dimethylpentane, 2,4-bis(diphenylphosphino)-3-ethylpentane, 2,4-bis(diphenylphosphino)-3,3-diethylpentane, 2,4-bis(diphenylphosphino)-3-n-propylpentane, 2,4-bis(diphenylphosphino)-3,3-di-n-propylpentane, 2,4-bis(diphenylphosphino)-3-isopropylpentane, 2,4-bis(diphenylphosphino)-3,3-diisopropylpentane, 2,4-bis(diphenylphosphino)-3-ethyl-3-methylpentane, 2,4-bis(diphenylphosphino)-3-methyl-3-n-propylpentane, 2,4-bis(diphenylphosphino)-3-methyl-3-isopropylpentane, 2,4-bis(diphenylphosphino)-3-ethyl-3-n-propylpentane, 2,4-bis(diphenylphosphino)-3-ethyl-3-isopropylpentane, 2,4-bis(diphenylphosphino)-3-n-propyl-3-isopropylpentane, etc.

(2) Illustrative of pentane derivatives having di-4-tolylphosphino groups at 2- and 4-positions are TolSKEWPHOS having one or two alkyl substituents with a carbon number of 1-3 at 3-position or having no alkyl substituent: 2,4-bis(di-4-tolylphosphino)pentane, 2,4-bis(di-4-tolylphosphino)-3-methylpentane, 2,4-bis(di-4-tolylphosphino)-3,3-dimethylpentane, 2,4-bis(di-4-tolylphosphino)-3-ethylpentane, 2,4-bis(di-4-tolylphosphino)-3,3-diethylpentane, 2,4-bis(di-4-tolylphosphino)-3-n-propylpentane, 2,4-bis(di-4-tolylphosphino)-3,3-di-n-propylpentane, 2,4-bis(di-4-tolylphosphino)-3-isopropylpentane, 2,4-bis(di-4-tolylphosphino)-3,3-diisopropylpentane, 2,4-bis(di-4-tolylphosphino)-3-ethyl-3-methylpentane, 2,4-bis(di-4-tolylphosphino)-3-methyl-3-n-propylpentane, 2,4-bis(di-4-tolylphosphino)-3-methyl-3-isopropylpentane, 2,4-bis(di-4-tolylphosphino)-3-ethyl-3-n-propylpentane, 2,4-bis(di-4-tolylphosphino)-3-ethyl-3-isopropylpentane, 2,4-bis(di-4-tolylphosphino)-3-n-propyl-3-isopropylpentane, etc.

(3) Illustrative of pentane derivatives having (4-t-butylphenyl)phosphino groups at 2- and 4-positions are 4-t-BuSKEW-PHOS having one or two alkyl substituents with a carbon number of 1-3 at 3-position or having no alkyl substituent: 2,4-bis[di(4-t-butylphenyl)phosphino]pentane, 2,4-bis[di(4-t-butylphenyl)phosphino]-3-methylpentane, 2,4-bis[di(4-t-butylphenyl)phosphino]-3,3-dimethylpentane, 2,4-bis[di(4-t-butylphenyl)phosphino]-3-ethylpentane, 2,4-bis[di(4-t-butylphenyl)phosphino]-3,3-diethylpentane, 2,4-bis[di(4-t-butylphenyl)phosphino]-3-n-propylpentane, 2,4-bis[di(4-t-butylphenyl)phosphino]-3,3-di-n-propylpentane, 2,4-bis[di(4-t-butylphenyl)phosphino]-3-isopropylpentane, 2,4-bis[di(4-t-butylphenyl)phosphino]-3,3-diisopropylpentane, 2,4-bis[di(4-t-butylphenyl)phosphino]-3-ethyl-3-methylpentane, 2,4-bis[di(4-t-butylphenyl)phosphino]-3-methyl-3-n-propylpentane, 2,4-bis[di(4-t-butylphenyl)phosphino]-3-methyl-3-isopropylpentane, 2,4-bis[di(4-t-butylphenyl)phosphino]-3-ethyl-3-n-propylpentane, 2,4-bis[di(4-t-butylphenyl)phosphino]-3-ethyl-3-isopropylpentane, 2,4-bis[di(4-t-butylphenyl)phosphino]-3-n-propyl-3-isopropyl pentane, etc.

(4) Illustrative of pentane derivatives having di-3,5-xylylphosphino groups at 2- and 4-positions are XylSKEW-PHOS having one or two alkyl substituents with a carbon number of 1-3 at 3-position or having no alkyl substituent: 2,4-bis(di-3,5-xylylphosphino)pentane, 2,4-bis(di-3,5-xylylphosphino)-3-methylpentane, 2,4-bis(di-3,5-xylylphosphino)-3,3-dimethylpentane, 2,4-bis(di-3,5-xylylphosphino)-3-ethylpentane, 2,4-bis(di-3,5-xylylphosphino)-3,3-diethylpentane, 2,4-bis(di-3,5-xylylphosphino)-3-n-propylpentane, 2,4-bis(di-3,5-xylylphosphino)-3,3-di-n-propylpentane, 2,4-bis(di-3,5-xylylphosphino)-3-isopropylpentane, 2,4-bis(di-3,5-xylylphosphino)-3,3-diisopropylpentane, 2,4-bis(di-3,5-xylylphosphino)-3-ethyl-3-methylpentane, 2,4-bis(di-3,5-xylylphosphino)-3-methyl-3-n-propylpentane, 2,4-bis(di-3,5-xylylphosphino)-3-methyl-3-isopropylpentane, 2,4-bis(di-3,5-xylylphosphino)-3-ethyl-3-n-propylpentane, 2,4-bis(di-3,5-xylylphosphino)-3-ethyl-3-isopropylpentane, 2,4-bis(di-3,5-xylylphosphino)-3-n-propyl-3-isopropylpentane, etc.

(5) Illustrative of pentane derivatives having (3,5-diethylphenyl)phosphino groups at 2- and 4-positions are 3,5-diEtSKEWPHOS having one or two alkyl substituents with a carbon number of 1-3 at 3-position or having no alkyl substituent: 2,4-bis[bis(3,5-diethylphenyl)phosphino]pentane, 2,4-bis[bis(3,5-diethylphenyl)phosphino]-3-methylpentane, 2,4-bis[bis(3,5-diethylphenyl)phosphino]-3,3-dimethylpentane, 2,4-bis[bis(3,5-diethylphenyl)phosphino]-3-ethylpentane, 2,4-bis[bis(3,5-diethylphenyl)phosphino]-3,3-diethylpentane, 2,4-bis[bis(3,5-diethylphenyl)phosphino]-3-n-propylpentane, 2,4-bis[bis(3,5-diethylphenyl)phosphino]-3,3-di-n-propylpentane, 2,4-bis[bis(3,5-diethylphenyl)phosphino]-3-isopropylpentane, 2,4-bis[bis(3,5-diethylphenyl)phosphino]-3,3-diisopropylpentane, 2,4-bis[bis(3,5-diethylphenyl)phosphino]-3-ethyl-3-methylpentane, 2,4-bis[bis(3,5-diethylphenyl)phosphino]-3-methyl-3-n-propylpentane, 2,4-bis[bis(3,5-diethylphenyl)phosphino]-3-methyl-3-isopropylpentane, 2,4-bis[bis(3,5-diethylphenyl)phosphino]-3-ethyl-3-n-propylpentane, 2,4- bis[bis(3,5-diethylphenyl)phosphino]-3-ethyl-3-isopropylpentane, 2,4-bis[bis(3,5-diethylphenyl)phosphino]-3-n-propyl-3-isopropylpentane, etc.

(6) Illustrative of 1,3-diphenylpropane derivatives having diphenylphosphino groups at 1- and 3-positions are those having one or two alkyl substituents with a carbon number of 1-3 at 2-position, such as 1,3-bis(diphenylphosphino)-1,3-diphenyl-2-methylpropane, 1,3-bis(diphenylphosphino)-1,3-diphenyl-2,2-dimethylpropane, 1,3-bis(diphenylphosphino)-1,3-diphenyl-2-ethylpropane, 1,3-bis(diphenylphosphino)-1,3-diphenyl-2,2-diethylpropane, 1,3-bis(diphenylphosphino)-1,3-diphenyl-2-n-propylpropane, 1,3-bis(diphenylphosphino)-1,3-diphenyl-2,2-di-n-propylpropane, 1,3-bis(diphenylphosphino)-1,3-diphenyl-2-isopropylpropane, 1,3-bis(diphenylphosphino)-1,3-diphenyl-2,2-diisopropylpropane, 1,3-bis(diphenylphosphino)-1,3-diphenyl-2-ethyl-2-methylpropane, 1,3-bis(diphenylphosphino)-1,3-diphenyl-2-methyl-2-n-propylpropane, 1,3-bis(diphenylphosphino)-1,3-diphenyl-2-methyl-2-isopropylpropane, 1,3-bis(diphenylphosphino)-1,3-diphenyl-2-ethyl-2-n-propylpropane, 1,3-bis(diphenylphosphino)-1,3-diphenyl-2-ethyl-2-isopropylpropane, 1,3-bis(diphenylphosphino)-1,3-diphenyl-2-n-propyl-2-isopropylpropane.

(7) Illustrative of 1,3-diphenylpropane derivatives having di-4-tolylphosphino groups at 1- and 3-positions are those having one or two alkyl substituents with a carbon number of 1-3 at 2-position or having no alkyl substituent, such as 1,3-bis(di-4-tolylphosphino)-1,3-diphenylpropane, 1,3-bis(di-4-tolylphosphino)-1,3-diphenyl-2-methylpropane, 1,3-bis(di-4-tolylphosphino)-1,3-diphenyl-2,2-dimethylpropane, 1,3-bis(di-4-tolylphosphino)-1,3-diphenyl-2-ethylpropane, 1,3-bis(di-4-tolylphosphino)-1,3-diphenyl-2,2-diethylpropane, 1,3-bis(di-4-tolylphosphino)-1,3-diphenyl-2-n-propylpropane, 1,3-bis(di-4-tolylphosphino)-1,3-diphenyl-2,2-di-n-propylpropane, 1,3-bis(di-4-tolylphosphino)-1,3-diphenyl-2-isopropylpropane, 1,3-bis(di-4-tolylphosphino)-1,3-diphenyl-2,2-diisopropylpropane, 1,3-bis(di-4-tolylphosphino)-1,3-diphenyl-2-ethyl-2-methylpropane, 1,3-bis(di-4-tolylphosphino)-1,3-diphenyl-2-methyl-2-n-propylpropane, 1,3-bis-(di-4-tolylphosphino)-1,3-diphenyl-2-methyl-2-isopropylpropane, 1,3-bis(di-4-tolylphosphino)-1,3-diphenyl-2-ethyl-2-n-propylpropane, 1,3-bis(di-4-tolylphosphino)-1,3-diphenyl-2-ethyl-2-isopropylpropane, 1,3-bis(di-4-tolylphosphino)-1,3-diphenyl-2-n-propyl-2-isopropylpropane.

(8) Illustrative of 1,3-diphenylpropane derivatives having di(4-t-butylphenyl)phosphino groups at 1- and 3-positions are those having one or two alkyl substituents with a carbon number of 1-3 at 2-position or having no alkyl substituent, such as 1,3-bis[di(4-t-butylphenyl)phosphino]-1,3-diphenylpropane, 1,3-bis[di(4-t-butylphenyl)phosphino]-1,3-diphenyl-2-methylpropane, 1,3-bis[di(4-t-butylphenyl)phosphino]-1,3-diphenyl-2,2-dimethylpropane, 1,3-bis[di(4-t-butylphenyl)phosphino]-1,3-diphenyl-2-ethylpropane, 1,3-bis[di(4-t-butylphenyl)phosphino]-1,3-diphenyl-2,2-diethylpropane, 1,3-bis[di(4-t-butylphenyl)phosphino]-1,3-diphenyl-2-n-propylpropane, 1,3-bis[di(4-t-butylphenyl)phosphino]-1,3-diphenyl-2,2-di-n-propylpropane, 1,3-bis[di(4-t-butylphenyl)phosphino]-1,3-diphenyl-2-isopropylpropane, 1,3-bis[di(4-t-butylphenyl)phosphino]-1,3-diphenyl-2,2-diisopropylpropane, 1,3-bis[di(4-t-butylphenyl)phosphino]-1,3-diphenyl-2-ethyl-2-methylpropane, 1,3-bis[di(4-t-butylphenyl)phosphino]-1,3-diphenyl-2-methyl-2-n-propylpropane, 1,3-bis[di(4-t-butylphenyl)phosphino]-1,3-diphenyl-2-methyl-2-isopropylpropane, 1,3-bis[di(4-t-butylphenyl)phosphino]-1,3-diphenyl-2-ethyl-2-n-propylpropane, 1,3-bis[di(4-t-butylphenyl)phosphino]-1,3-diphenyl-2-ethyl-2-isopropylpropane, 1,3-bis[di(4-t-butylphenyl)phosphino]-1,3-diphenyl-2-n-propyl-2-isopropylpropane.

(9) Illustrative of 1,3-diphenylpropane derivatives having di-3,5-xylylphosphino groups at 1- and 3-positions are those having one or two alkyl substituents with a carbon number of 1-3 at 2-position or having no alkyl substituent, such as 1,3-bis(di-3,5-xylylphosphino)-1,3-diphenylpropane, 1,3-bis(di-3,5-xylylphosphino)-1,3-diphenyl-2-methylpropane, 1,3-bis(di-3,5-xylylphosphino)-1,3-diphenyl-2,2-dimethylpropane, 1,3-bis(di-3,5-xylylphosphino)-1,3-diphenyl-2-ethylpropane, 1,3-bis(di-3,5-xylylphosphino)-1,3-diphenyl-2,2-diethylpropane, 1,3-bis(di-3,5-xylylphosphino)-1,3-diphenyl-2-n-propylpropane, 1,3-bis(di-3,5-xylylphosphino)-1,3-diphenyl-2,2-di-n-propylpropane, 1,3-bis(di-3,5-xylylphosphino)-1,3-diphenyl-2-isopropylpropane, 1,3-bis(di-3,5-xylylphosphino)-1,3-diphenyl-2,2-diisopropylpropane, 1,3-bis(di-3,5-xylylphosphino)-1,3-diphenyl-2-ethyl-2-methylpropane, 1,3-bis(di-3,5-xylylphosphino)-1,3-diphenyl-2-methyl-2-n-propylpropane, 1,3-bis(di-3,5-xylylphosphino)-1,3-diphenyl-2-methyl-2-isopropylpropane, 1,3-bis(di-3,5-xylylphosphino)-1,3-diphenyl-2-ethyl-2-n-propylpropane, 1,3-bis(di-3,5-xylylphosphino)-1,3-diphenyl-2-ethyl-2-isopropylpropane, 1,3-bis(di-3,5-xylylphosphino)-1,3-diphenyl-2-n-propyl-2-isopropylpropane.

(10) Illustrative of 1,3-diphenylpropane derivatives having bis(3,5-diethylphenyl)phosphino groups at 1- and 3-positions are those having one or two alkyl substituents with a carbon number of 1-3 at 2-position or having no alkyl substituent, such as 1,3-bis[bis(3,5-diethylphenyl)phosphino]-1,3-diphenylpropane, 1,3-bis[bis(3,5-diethylphenyl)phosphino]-1,3-diphenyl-2-methylpropane, 1,3-bis[bis(3,5-diethylphenyl)phosphino]-1,3-diphenyl-2,2-dimethylpropane, 1,3-bis[bis(3,5-diethylphenyl)phosphino]-1,3-diphenyl-2-ethylpropane, 1,3-bis[bis(3,5-diethylphenyl)phosphino]-1,3-diphenyl-2,2-diethylpropane, 1,3-bis[bis(3,5-diethylphenyl)phosphino]-1,3-diphenyl-2-n-propylpropane, 1,3-bis[bis(3,5-diethylphenyl)phosphino]-1,3-diphenyl-2,2-di-n-propylpropane, 1,3-bis[bis(3,5-diethylphenyl)phosphino]-1,3-diphenyl-2-isopropylpropane, 1,3-bis[bis(3,5-diethylphenyl)phosphino]-1,3-diphenyl-2,2-diisopropylpropane, 1,3-bis[bis(3,5-diethylphenyl)phosphino]-1,3-diphenyl-2-ethyl-2-methylpropane, 1,3-bis[bis(3,5-diethylphenyl)phosphino]-1,3-diphenyl-2-methyl-2-n-propylpropane, 1,3-bis[bis(3,5-diethylphenyl)phosphino]-1,3-diphenyl-2-methyl-2-isopropylpropane, 1,3-bis[bis(3,5-diethylphenyl)phosphino]-1,3-diphenyl-2-ethyl-2-n-propylpropane, 1,3-bis[bis(3,5-diethylphenyl)phosphino]-1,3-diphenyl-2-ethyl-2-isopropylpropane, 1,3-bis[bis(3,5-diethylphenyl)phosphino]-1,3-diphenyl-2-n-propyl-2-isopropylpropane. In particular, SKEWPHOS, TolSKEWPHOS, 3,5-diEtSKEWPHOS, 4-t-BuSKEWPHOS and XylSKEWPHOS are preferable. However, of course, optically active diphosphine compounds which can be used in the invention are not limited thereto in any way.

In the following general formula (3) or (4) which represents an amine ligand or an optically active diamine compound denoted by B in the optically active ruthenium complex of general formula (1),

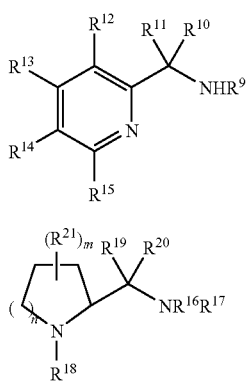

(3)

(4)

in general formula (3), $R^9$ denotes a hydrogen atom, an alkyl group having a carbon number of 1-20 or a cyclic hydrocarbon group which may have one or more substituents; $R^{10}$ and $R^{11}$ may be mutually identical or different and denote a hydrogen atom, an alkyl group having a carbon number of 1-20 or a cyclic hydrocarbon group which may have one or more substituents, $R^{10}$ and $R^{11}$ may be mutually bonded to form a saturated or unsaturated hydrocarbon group which may have one or more substituents such as alkyl, alkenyl, cycloalkyl, aryl, alkoxy, ester, acyloxy, halogen atoms, nitro, or cyano; $R^{12}$, $R^{13}$, $R^{14}$ and $R^{15}$ may be mutually identical or different and denote a hydrogen atom, an alkyl group having a carbon number of 1-20 or a cyclic hydrocarbon group which may have one or more substituents, $R^{12}$ and $R^{13}$, $R^{13}$ and $R^{14}$, or $R^{14}$ and $R^{15}$ may be mutually bonded to form a saturated or unsaturated hydrocarbon group, or to form a saturated or unsaturated hydrocarbon group containing N. Here, said $R^9$ representing a hydrogen atom, an alkyl group having a carbon number of 1-20 or a cyclic hydrocarbon group which may have one or more substituents, may be a hydrogen atom, a saturated or unsaturated, aliphatic or alicyclic hydrocarbon group, a monocyclic or polycyclic, aromatic or araliphatic hydrocarbon group, or any species of these hydrocarbon groups having one or more substituents. Examples include hydrogen atoms, hydrocarbon groups such as alkyl, alkenyl, cycloalkyl, cycloalkenyl, phenyl, naphthyl and phenylalkyl, and said hydrocarbon groups further having various acceptable substituents such as alkyl, alkenyl, cycloalkyl, aryl, alkoxy, ester, acyloxy, halogen atoms, nitro group and cyano group. Among them, hydrogen atoms and alkyl, phenyl and phenylalkyl groups are preferred, and hydrogen atoms are particularly preferred. Said $R^{10}$ and $R^{11}$ which may be mutually identical or different, representing a hydrogen atom, an alkyl group having a carbon number of 1-20 or a cyclic hydrocarbon group which may have one or more substituents, may be a hydrogen atom, a saturated or unsaturated, aliphatic or alicyclic hydrocarbon group, a monocyclic and aromatic or araliphatic hydrocarbon group, or any species of these hydrocarbon groups having one or more substituents. Examples include hydrogen atoms, hydrocarbon groups such as alkyl, alkenyl, cycloalkyl, cycloalkenyl, phenyl, naphthyl and phenylalkyl, and said hydrocarbon groups further having various acceptable substituents such as alkyl, alkenyl, cycloalkyl, aryl, alkoxy, ester, acyloxy, halogen atoms, nitro group and cyano group. Among them, hydrogen atoms and alkyl, phenyl and phenylalkyl groups are preferred; it is particularly preferred that all substituents are hydrogen atoms. In case that $R^{10}$ and $R^{11}$ are mutually bonded to form a saturated or unsaturated hydrocarbon group which may have one or more substituents such as alkyl, alkenyl, cycloalkyl, aryl, alkoxy, ester, acyloxy, halogen atoms, nitro, or cyano, $R^{10}$ and $R^{11}$ may be a saturated or unsaturated, aliphatic or alicyclic hydrocarbon group, a monocyclic and aromatic or araliphatic hydrocarbon group. Examples include hydrocarbon groups such as alkyl, alkenyl, cycloalkyl, cycloalkenyl, phenyl and naphthyl. Said $R^{12}$, $R^{13}$, $R^{14}$ and $R^{15}$ which may be mutually identical or different, representing a hydrogen atom, an alkyl group having a carbon number of 1-20 or a cyclic hydrocarbon group which may have one or more substituents, may be a hydrogen atom, a saturated or unsaturated, aliphatic or alicyclic hydrocarbon group, a monocyclic and aromatic or araliphatic hydrocarbon group, or any species of these hydrocarbon groups having one or more substituents. Examples include hydrogen atoms, hydrocarbon groups such as alkyl, alkenyl, cycloalkyl, cycloalkenyl, phenyl, naphthyl and phenylalkyl, and said hydrocarbon groups further having various acceptable substituents such as alkyl, alkenyl, cycloalkyl, aryl, alkoxy, ester, acyloxy, halogen atoms, nitro group and cyano group. Among them, hydrogen atoms, alkyl, phenyl and phenylalkyl are preferred, and hydrogen atoms are particularly preferred.

Said $R^{12}$ and $R^{13}$, $R^{13}$ and $R^{14}$, or $R^{14}$ and $R^{15}$ representing those which may be mutually bonded to form a saturated or unsaturated hydrocarbon group, may be a saturated or unsaturated, aliphatic or alicyclic hydrocarbon group, a monocyclic and aromatic or araliphatic hydrocarbon group, a heterocyclic group, or any species of these hydrocarbon groups or heterocyclic groups having one or more substituents, which may contain an N atom. Examples include hydrocarbon groups such as alkyl, alkenyl, cycloalkyl, cycloalkenyl, phenyl, naphthyl, phenylalkyl and pyridine, and said hydrocarbon groups further having various acceptable substituents such as alkyl, alkenyl, cycloalkyl, aryl, alkoxy, ester, acyloxy, halogen atoms, nitro group and cyano group.

Among them, alkyl and alkenyl are preferred, and alkenyl is particularly preferred.

Thus, examples of the diamine compound of general formula (3) include:

(1) those wherein all the substituents are hydrogen, such as PICA: 2-picolylamine, (2) those having a substituent in $R^9$, such as MePICA:2-(N-methylaminomethyl)pyridine, EtPICA:2-(N-ethylaminomethyl)pyridine, n-PrPICA:2-(N-n-propylaminomethyl)pyridine, i-PrPICA:2-(N-isopropylaminomethyl)pyridine, n-BtPICA:2-(N-n-butylaminomethyl)pyridine, t-BtPICA:2-(N-t-butylaminomethyl)pyridine, PhPICA:2-(N-phenylaminomethyl)pyridine, BnPICA:2-(N-benzylaminomethyl)pyridine, (3) those having one or more substituents in $R^{10}$ and $R^{11}$, such as 2-(1-aminoethyl)pyridine, 2-(1-phenylaminomethyl)pyridine, 2-(1-methyl-1-aminoethyl)pyridine, 2-(1-phenyl-1-aminoethyl)pyridine, 2-(1,1-diphenylaminomethyl)pyridine, (4) those having a substituent on the pyridine ring, such as 3-Me-PICA:2-(aminomethyl)-3-methylpyridine, 4-Me-PICA:2-(aminomethyl)-4-methylpyridine, 5-Me-PICA:2-(aminomethyl)-5-methylpyridine, 6-Me-PICA:2-(aminomethyl)-6-methylpyridine, 3-Et-PICA:2-(aminomethyl)-3-ethylpyridine, 4-Et-PICA:2-(aminomethyl)-4-ethylpyridine, 5-Et-PICA:2-(aminomethyl)-5-ethylpyridine, 6-Et-PICA:2-(aminomethyl)-6-ethylpyridine, 3-n-Pr-PICA:2-(aminomethyl)-3-n-propylpyridine, 4-n-Pr-PICA:2-(aminomethyl)-4-n-propylpyridine, 5-n-Pr-PICA:2-(aminomethyl)-5-n-propylpyridine, 6-n-Pr-PICA:2-(aminomethyl)-6-n-propylpyridine, 3-i-Pr-PICA:2-(aminomethyl)-3-i-propylpyridine, 4-i-Pr-PICA:2-(aminomethyl)-4-i- propylpyridine, 5-i-Pr-PICA:2-(aminomethyl)-5-i-propylpyridine, 6-i-Pr-PICA:2-(aminomethyl)-6-i-propylpyridine, 3-Ph-PICA:2-(aminomethyl)-3-phenylpyridine, 4-Ph-PICA:2-(aminomethyl)-4-phenylpyridine, 5-Ph-PICA:2-(aminomethyl)-5-phenylpyridine, 6-Ph-PICA:2-(aminomethyl)-6-phenylpyridine, 3-Bn-PICA:2-(aminomethyl)-3-benzylpyridine, 4-Bn-PICA:2-(aminomethyl)-4-benzylpyridine, 5-Bn-PICA:2-(aminomethyl)-5-benzylpyridine, 6-Bn-PICA:2-(aminomethyl)-6-benzylpyridine, (5) 2-quinoline derivatives wherein $R^9$ is hydrogen, such as AMQ:2-aminomethylquinoline, (6) 2-quinoline derivatives having a substituent in $R^9$, such as MeAMQ:2-(N-methylaminomethyl)quinoline, EtAMQ:2-(N-ethylaminomethyl)quinoline, n-PrAMQ:2-(N-n-propylaminomethyl)quinoline, i-PrAMQ:2-(N-isopropylaminomethyl)quinoline, n-BuAMQ:2-(N-n-butylaminomethyl)quinoline, t-BuAMQ:2-(N-t-butylaminomethyl)quinoline, PhAMQ:2-(N-phenylaminomethyl)quinoline, BnAMQ:2-(N-benzylaminomethyl)quinoline, (7) 2-quinoline derivatives having one or more substituents in $R^{10}$ and $R^{11}$, such as 2-(1-aminoethyl)quinoline, 2-(1-phenylaminomethyl)quinoline, 2-(1-methyl-1-aminoethyl)quinoline, 2-(1-phenyl-1-aminoethyl)quinoline, 2-(1,1-diphenylaminomethyl)quinoline, (8) 2-quinoline derivatives having a substituent on the ring, such as 3-MeAMQ:2-(aminomethyl)-3-methylquinoline, 4-MeAMQ:2-(aminomethyl)-4-methylquinoline, 5-MeAMQ:2-(aminomethyl)-5-methylquinoline, 6-MeAMQ:2-(aminomethyl)-6-methylquinoline, 7-MeAMQ:2-(aminomethyl)-7-methylquinoline, 8-MeAMQ:2-(aminomethyl)-8-methylquinoline, 3-EtAMQ:2-(aminomethyl)-3-ethylquinoline, 4-EtAMQ:2-(aminomethyl)-4-ethylquinoline, 5-EtAMQ:2-(aminomethyl)-5-ethylquinoline, 6-EtAMQ:2-(aminomethyl)-6-ethylquinoline, 7-EtAMQ:2-(aminomethyl)-7-ethylquinoline, 8-EtAMQ:2-(aminomethyl)-8-ethylquinoline, 3-n-PrAMQ:2-(aminomethyl)-3-n-propylquinoline, 4-n-PrAMQ:2-(aminomethyl)-4-n-propylquinoline, 5-n-PrAMQ:2-(aminomethyl)-5-n-propylquinoline, 6-n-PrAMQ:2-(aminomethyl)-6-n-propylquinoline, 7-n-PrAMQ:2-(aminomethyl)-7-n-propylquinoline, 8-n-PrAMQ:2-(aminomethyl)-8-n-propylquinoline, 3-i-PrAMQ:2-(aminomethyl)-3-i-propylquinoline, 4-i-PrAMQ:2-(aminomethyl)-4-i-propylquinoline, 5-i-PrAMQ:2-(aminomethyl)-5-i-propylquinoline, 6-i-PrAMQ:2-(aminomethyl)-6-i-propylquinoline, 7-i-PrAMQ:2-(aminomethyl)-7-i-propylquinoline, 8-i-PrAMQ:2-(aminomethyl)-8-i-propylquinoline, 3-n-BuAMQ:2-(aminomethyl)-3-n-butylquinoline, 4-n-BuAMQ:2-(aminomethyl)-4-n-butylquinoline, 5-n-BuAMQ:2-(aminomethyl)-5-n-butylquinoline, 6-n-BuAMQ:2-(aminomethyl)-6-n-butylquinoline, 7-n-BuAMQ:2-(aminomethyl)-7-n-butylquinoline, 8-n-BuAMQ:2-(aminomethyl)-8-n-butylquinoline, 3-t-BuAMQ:2-(aminomethyl)-3-t-butylquinoline, 4-t-BuAMQ:2-(aminomethyl)-4-t-butylquinoline, 5-t-BuAMQ:2-(aminomethyl)-5-t-butylquinoline, 6-t-BuAMQ:2-(aminomethyl)-6-t-butylquinoline, 7-t-BuAMQ:2-(aminomethyl)-7-t-butylquinoline, 8-t-BuAMQ:2-(aminomethyl)-8-t-butylquinoline, 3-PhAMQ:2-(aminomethyl)-3-phenylquinoline, 4-PhAMQ:2-(aminomethyl)-4-phenylquinoline, 5-PhAMQ:2-(aminomethyl)-5-phenylquinoline, 6-PhAMQ:2-(aminomethyl)-6-phenylquinoline, 7-PhAMQ:2-(aminomethyl)-7-phenylquinoline, 8-PhAMQ:2-(aminomethyl)-8-phenylquinoline, 3-BnAMQ:2-(aminomethyl)-3-benzylquinoline, 4-BnAMQ:2-(aminomethyl)-4-benzylquinoline, 5-BnAMQ:2-(aminomethyl)-5-benzylquinoline, 6-BnAMQ:2-(aminomethyl)-6-benzylquinoline, 7-BnAMQ:2-(aminomethyl)-7-benzylquinoline, 8-BnAMQ:2-(aminomethyl)-8-benzylquinoline, (9) 1-isoquinoline derivatives wherein $R^9$ is hydrogen, such as AM-1-IQ:1-aminomethylisoquinoline,

(10) 1-isoquinoline derivatives having a substituent in $R^9$, such as MeAM-1-IQ:1-(N-methylaminomethyl)isoquinoline, EtAM-1-IQ:1-(N-ethylaminomethyl)isoquinoline, n-PrAM-1-IQ:1-(N-n-propylaminomethyl)isoquinoline, i-PrAM-1-IQ:1-(N-isopropylaminomethyl)isoquinoline, n-BuAM-1-IQ:1-(N-n-butylaminomethyl)isoquinoline, t-BuAM-1-IQ:1-(N-t-butylaminomethyl)isoquinoline, PhAM-1-IQ:1-(N-phenylaminomethyl)isoquinoline, BnAM-1-IQ:1-(N-benzylaminomethyl)isoquinoline,

(11) 1-isoquinoline derivatives having one or more substituents in $R^{10}$ and $R^{11}$, such as 1-(1-aminoethyl)isoquinoline, 1-(1-phenylaminomethyl)isoquinoline, 1-(1-methylaminoethyl)isoquinoline, 1-(1-phenyl-1-aminoethyl)isoquinoline, 1-(1,1-diphenylaminomethyl)isoquinoline,

(12) 1-isoquinoline derivatives having a substituent on the ring, such as 3-MeAM-1-IQ:1-(aminomethyl)-3-methylisoquinoline, 4-MeAM-1-IQ:1-(aminomethyl)-4-methylisoquinoline, 5-MeAM-1-IQ:1-(aminomethyl)-5-methylisoquinoline, 6-MeAM-1-IQ:1-(aminomethyl)-6-methylisoquinoline, 7-MeAM-1-IQ:1-(aminomethyl)-7-methylisoquinoline, 8-MeAM-1-IQ:1-(aminomethyl)-8-methylisoquinoline, 3-EtAM-1-IQ:1-(aminomethyl)-3-ethylisoquinoline, 4-EtAM-1-IQ:1-(aminomethyl)-4-ethylisoquinoline, 5-EtAM-1-IQ:1-(aminomethyl)-5-ethylisoquinoline, 6-EtAM-1-IQ:1-(aminomethyl)-6-ethylisoquinoline, 7-EtAM-1-IQ:1-(aminomethyl)-7-ethylisoquinoline, 8-EtAM-1-IQ:1-(aminomethyl)-8-ethylisoquinoline, 3-n-PrAM-1-IQ:1-(aminomethyl)-3-n-propylisoquinoline, 4-n-PrAM-1-IQ:1-(aminomethyl)-4-n-propylisoquinoline, 5-n-PrAM-1-IQ:1-(aminomethyl)-5-n-propylisoquinoline, 6-n-PrAM-1-IQ:1-(aminomethyl)-6-n-propylisoquinoline, 7-n-PrAM-1-IQ:1-(aminomethyl)-7-n-propylisoquinoline, 8-n-PrAM-1-IQ:1-(aminomethyl)-8-n-propylisoquinoline, 3-i-PrAM-1-IQ:1-(aminomethyl)-3-i-propylisoquinoline, 4-i-PrAM-1-IQ:1-(aminomethyl)-4-i-propylisoquinoline, 5-i-PrAM-1-IQ:1-(aminomethyl)-5-i-propylisoquinoline, 6-i-PrAM-1-IQ:1-(aminomethyl)-6-i-propylisoquinoline, 7-i-PrAM-1-IQ:1-(aminomethyl)-7-i-propylisoquinoline, 8-i-PrAM-1-IQ:1-(aminomethyl)-8-i-propylisoquinoline, 3-n-BuAM-1-IQ:1-(aminomethyl)-3-n-butylisoquinoline, 4-n-BuAM-1-IQ:1-(aminomethyl)-4-n-butylisoquinoline, 5-n-BuAM-1-IQ:1-(aminomethyl)-5-n-butylisoquinoline, 6-n-BuAM-1-IQ:1-(aminomethyl)-6-n-butylisoquinoline, 7-n-BuAM-1-IQ:1-(aminomethyl)-7-n-butylisoquinoline, 8-n-BuAM-1-IQ:1-(aminomethyl)-8-n-butylisoquinoline, 3-t-BuAM-1-IQ:1-(aminomethyl)-3-t-butylisoquinoline, 4-t-BuAM-1-IQ:1-(aminomethyl)-4-t-butylisoquinoline, 5-t-BuAM-1-IQ:1-(aminomethyl)-5-t-butylisoquinoline, 6-t-BuAM-1-IQ:1-(aminomethyl)-6-t-butylisoquinoline, 7-t-BuAM-1-IQ:1-(aminomethyl)-7-t-butylisoquinoline, 8-t-BuAM-1-IQ:1-(aminomethyl)-8-t-butylisoquinoline, 3-PhAM-1-IQ:1-(aminomethyl)-3-phenylisoquinoline, 4-PhAM-1-IQ:1-(aminomethyl)-4-phenylisoquinoline, 5-PhAM-1-IQ:1-(aminomethyl)-5-phenylisoquinoline, 6-PhAM-1-IQ:1-(aminomethyl)-6-phenylisoquinoline, 7-PhAM-1-IQ:1-(aminomethyl)-7-phenylisoquinoline, 8-PhAM-1-IQ:1-(aminomethyl)-8-phenylisoquinoline, 3-BnAM-1-IQ:1-(aminomethyl)-3- benzylisoquinoline, 4-BnAM-1-IQ:1-(aminomethyl)-4-benzylisoquinoline, 5-BnAM-1-IQ:1-(aminomethyl)-5-benzylisoquinoline, 6-BnAM-1-IQ:1-(aminomethyl)-6-benzylisoquinoline, 7-BnAM-1-IQ:1-(aminomethyl)-7-benzylisoquinoline, 8-BnAM-1-IQ:1-(aminomethyl)-8-benzylisoquinoline,

(13) 3-isoquinoline derivatives wherein $R^9$ is hydrogen, such as AM-3-IQ:3-aminomethylisoquinoline,

(14) 3-isoquinoline derivatives having a substituent in $R^9$, such as MeAM-3-IQ:3-(N-methylaminomethyl)isoquinoline, EtAM-3-IQ:3-(N-ethylaminomethyl)isoquinoline, n-PrAM-3-IQ:3-(N-n-propylaminomethyl)isoquinoline, i-PrAM-3-IQ:3-(N-isopropylaminomethyl)isoquinoline, n-BuAM-3-IQ:3-(N-n-butylaminomethyl)isoquinoline, t-BuAM-3-IQ:3-(N-t-butylaminomethyl)isoquinoline, PhAM-3-IQ:3-(N-phenylaminomethyl)isoquinoline, BnAM-3-IQ:3-(N-benzylaminomethyl)isoquinoline,

(15) 3-isoquinoline derivatives having one or more substituents in $R^{10}$ and $R^{11}$, such as 3-(1-aminoethyl)isoquinoline, 3-(1-phenylaminomethyl)isoquinoline, 3-(1-methyl-1-aminoethyl)isoquinoline, 3-(1-phenyl-1-aminoethyl)isoquinoline, 3-(1,1-diphenylaminomethyl)isoquinoline,

(16) 3-isoquinoline derivatives having a substituent on the ring, such as 1-MeAM-3-IQ:3-(aminomethyl)-1-methylisoquinoline, 4-MeAM-3-IQ:3-(aminomethyl)-4-methylisoquinoline, 5-MeAM-3-IQ:3-(aminomethyl)-5-methylisoquinoline, 6-MeAM-3-IQ:3-(aminomethyl)-6-methylisoquinoline, 7-MeAM-3-IQ:3-(aminomethyl)-7-methylisoquinoline, 8-MeAM-3-IQ:3-(aminomethyl)-8-methylisoquinoline, 1-EtAM-3-IQ:3-(aminomethyl)-1-ethylisoquinoline, 4-EtAM-3-IQ:3-(aminomethyl)-4-ethylisoquinoline, 5-EtAM-3-IQ:3-(aminomethyl)-5-ethylisoquinoline, 6-EtAM-3-IQ:3-(aminomethyl)-6-ethylisoquinoline, 7-EtAM-3-IQ:3-(aminomethyl)-7-ethylisoquinoline, 8-EtAM-3-IQ:3-(aminomethyl)-8-ethylisoquinoline, 1-n-PrAM-3-IQ:3-(aminomethyl)-1-n-propylisoquinoline, 4-n-PrAM-3-IQ:3-(aminomethyl)-4-n-propylisoquinoline, 5-n-PrAM-3-IQ:3-(aminomethyl)-5-n-propylisoquinoline, 6-n-PrAM-3-IQ:3-(aminomethyl)-6-n-propylisoquinoline, 7-n-PrAM-3-IQ:3-(aminomethyl)-7-n-propylisoquinoline, 8-n-PrAM-3-IQ:3-(aminomethyl)-8-n-propylisoquinoline, 1-i-PrAM-3-IQ:3-(aminomethyl)-1-i-propylisoquinoline, 4-i-PrAM-3-IQ:3-(aminomethyl)-4-i-propylisoquinoline, 5-i-PrAM-3-IQ:3-(aminomethyl)-5-i-propylisoquinoline, 6-i-PrAM-3-IQ:3-(aminomethyl)-6-i-propylisoquinoline, 7-i-PrAM-3-IQ:3-(aminomethyl)-7-i-propylisoquinoline, 8-i-PrAM-3-IQ:3-(aminomethyl)-8-i-propylisoquinoline, 1-n-BuAM-3-IQ:3-(aminomethyl)-1-n-butylisoquinoline, 4-n-BuAM-3-IQ:3-(aminomethyl)-4-n-butylisoquinoline, 5-n-BuAM-3-IQ:3-(aminomethyl)-5-n-butylisoquinoline, 6-n-BuAM-3-IQ:3-(aminomethyl)-6-n-butylisoquinoline, 7-n-BuAM-3-IQ:3-(aminomethyl)-7-n-butylisoquinoline, 8-n-BuAM-3-IQ:3-(aminomethyl)-8-n-butylisoquinoline, 1-t-BuAM-3-IQ:3-(aminomethyl)-1-t-butylisoquinoline, 4-t-BuAM-3-IQ:3-(aminomethyl)-4-t-butylisoquinoline, 5-t-BuAM-3-IQ:3-(aminomethyl)-5-t-butylisoquinoline, 6-t-BuAM-3-IQ:3-(aminomethyl)-6-t-butylisoquinoline, 7-t-BuAM-3-IQ:3-(aminomethyl)-7-t-butylisoquinoline, 8-t-BuAM-3-IQ:3-(aminomethyl)-8-t-butylisoquinoline, 1-PhAM-3-IQ:3-(aminomethyl)-1-phenylisoquinoline, 4-PhAM-3-IQ:3-(aminomethyl)-4-phenylisoquinoline, 5-PhAM-3-IQ:3-(aminomethyl)-5-phenylisoquinoline, 6-PhAM-3-IQ:3-(aminomethyl)-6-phenylisoquinoline, 7-PhAM-3-IQ:3-(aminomethyl)-7-phenylisoquinoline, 8-PhAM-3-IQ:3-(aminomethyl)-8-phenylisoquinoline, 1-BnAM-3-IQ:3-(aminomethyl)-1-benzylisoquinoline, 4-BnAM-3-IQ:3-(aminomethyl)-4-benzylisoquinoline, 5-BnAM-3-IQ:3-(aminomethyl)-5-benzylisoquinoline, 6-BnAM-3-IQ:3-(aminomethyl)-6-benzylisoquinoline, 7-BnAM-3-IQ:3-(aminomethyl)-7-benzylisoquinoline, 8-BnAM-3-IQ:3-(aminomethyl)-8-benzylisoquinoline. In particular, 2-(aminomethyl)-6-methylpyridine and 2-picolylamine are preferred.

In general formula (4), at least one of $R^{16}$, $R^{17}$ and $R^{18}$ is a hydrogen atom, $R^{16}$ and $R^{17}$ may be mutually identical or different and denote a hydrogen atom, an alkyl group having a carbon number of 1-20 or a cyclic hydrocarbon group which may have one or more substituents, $R^{16}$ and $R^{17}$ may be mutually bonded to form a ring containing N, $R^{18}$ denotes a hydrogen atom, an alkyl group having a carbon number of 1-20 or a cyclic hydrocarbon group which may have one or more substituents; $R^{19}$ and $R^{20}$ may be mutually identical or different and denote a hydrogen atom, an alkyl group having a carbon number of 1-20 or a cyclic hydrocarbon group which may have one or more substituents, $R^{19}$ and $R^{20}$ may be mutually bonded to form a saturated or unsaturated hydrocarbon group which may have one or more substituents such as alkyl, alkenyl, cycloalkyl, aryl, alkoxy, ester, acyloxy, halogen atoms, nitro, or cyano; $R^{21}$ may be mutually identical or different and denotes a hydrogen atom, an alkyl group having a carbon number of 1-20 or a cyclic hydrocarbon group which may have one or more substituents, and adjacent $R^{21}$ may be mutually bonded to form a saturated or unsaturated hydrocarbon group; m denotes an integer of 1-10; n denotes an integer of 1-3. Said $R^{16}$ and $R^{17}$ which may be mutually identical or different, representing a hydrogen atom, an alkyl group having a carbon number of 1-20 or a cyclic hydrocarbon group which may have one or more substituents, may be a hydrogen atom, a saturated or unsaturated, aliphatic or alicyclic hydrocarbon group, a monocyclic or polycyclic, aromatic or araliphatic hydrocarbon group, or any species of these hydrocarbon groups having one or more substituents. Examples include hydrogen atoms, hydrocarbon groups such as alkyl, alkenyl, cycloalkyl, cycloalkenyl, phenyl, naphthyl and phenylalkyl, and said hydrocarbon groups further having various acceptable substituents such as alkyl, alkenyl, cycloalkyl, aryl, alkoxy, ester, acyloxy, halogen atoms, nitro group and cyano group. Among them, hydrogen atoms, alkyl, phenyl, phenylalkyl, cyclic alkylene, and alkenylene groups are preferred; it is particularly preferred that all substituents are hydrogen atoms. In addition, $R^{16}$ and $R^{17}$ representing those which may be mutually bonded to form a ring containing N, may be a saturated or unsaturated, aliphatic or alicyclic hydrocarbon group, a monocyclic and aromatic or araliphatic hydrocarbon group, or any species of these hydrocarbon groups having one or more substituents. Examples include hydrocarbon groups such as alkyl, alkenyl, cycloalkyl, cycloalkenyl, phenyl, naphthyl and phenylalkyl, and said hydrocarbon groups further having various acceptable substituents such as alkyl, alkenyl, cycloalkyl, aryl, alkoxy, ester, acyloxy, halogen atoms, nitro group and cyano group.

Among them, alkyl and alkenyl are preferred, and alkyl is particularly preferred.

Said $R^{18}$ representing a hydrogen atom, an alkyl group having a carbon number of 1-20 or a cyclic hydrocarbon group which may have one or more substituents, may be a hydrogen atom, a saturated or unsaturated, aliphatic or alicyclic hydrocarbon group, a monocyclic or polycyclic, aromatic or araliphatic hydrocarbon group, or any species of these hydrocarbon groups having one or more substituents. Examples include hydrogen atoms, hydrocarbon groups such as alkyl, alkenyl, cycloalkyl, cycloalkenyl, phenyl, naphthyl and phenylalkyl, and said hydrocarbon groups further having various acceptable substituents such as alkyl, alkenyl, cycloalkyl, aryl, alkoxy, ester, acyloxy, halogen atoms, nitro group and cyano group. Among them, hydrogen atoms, alkyl, phenyl and phenylalkyl groups are preferred, and hydrogen atoms are particularly preferred. $R^{19}$ and $R^{20}$ which may be mutually identical or different, representing a hydrogen atom, an alkyl group having a carbon number of 1-20 or a cyclic hydrocarbon group which may have one or more substituents, may be a hydrogen atom, a saturated or unsaturated, aliphatic or alicyclic hydrocarbon group, a monocyclic or polycyclic, aromatic or araliphatic hydrocarbon group, or any species of these hydrocarbon groups having one or more substituents. Examples include hydrogen atoms, hydrocarbon groups such as alkyl, alkenyl, cycloalkyl, cycloalkenyl, phenyl, naphthyl and phenylalkyl, and said hydrocarbon groups further having various acceptable substituents such as alkyl, alkenyl, cycloalkyl, aryl, alkoxy, ester, acyloxy, halogen atoms, nitro group and cyano group. In addition, $R^{19}$ and $R^{20}$ are those which may be mutually bonded to form a saturated or unsaturated hydrocarbon group which may have one or more substituents such as alkyl, alkenyl, cycloalkyl, aryl, alkoxy, ester, acyloxy, halogen atoms, nitro, or cyano. Among these substituents, hydrogen atoms, alkyl, phenyl and phenylalkyl groups are preferred, and hydrogen atoms are particularly preferred.

Said $R^{21}$ which may be mutually identical or different, representing a hydrogen atom, an alkyl group having a carbon number of 1-20 or a cyclic hydrocarbon group which may have one or more substituents, may be 2-aminomethylpyrrolidine, 2-aminomethylpiperidine, and 2-(aminomethyl)homopiperidine, wherein 1-10 substituents of a hydrogen atom, a saturated or unsaturated, aliphatic or alicyclic hydrocarbon group, a monocyclic or polycyclic, aromatic or araliphatic hydrocarbon group, or any species of these hydrocarbon groups having one or more substituents may be present on the ring. Examples include hydrogen atoms, hydrocarbon groups such as alkyl, alkenyl, cycloalkyl, cycloalkenyl, phenyl, naphthyl and phenylalkyl, and said hydrocarbon groups further having various acceptable substituents such as alkyl, alkenyl, cycloalkyl, aryl, alkoxy, ester, acyloxy, halogen atoms, nitro group and cyano group. In addition, adjacent $R^{21}$ which may be mutually bonded to form a saturated or unsaturated hydrocarbon group may be a saturated or unsaturated, aliphatic or alicyclic hydrocarbon group, a monocyclic or polycyclic or araliphatic hydrocarbon group, or any species of these hydrocarbon groups having one or more substituents. Examples include hydrocarbon groups such as alkyl, alkenyl, cycloalkyl, cycloalkenyl, phenyl, naphthyl and phenylalkyl, and said hydrocarbon groups further having various acceptable substituents such as alkyl, alkenyl, cycloalkyl, aryl, alkoxy, ester, acyloxy, halogen atoms, nitro group and cyano group.

Thus, examples of the diamine compound of general formula (4) include:

(1) those wherein all substituents are hydrogen, such as AMPY:2-aminomethylpyrrolidine, AMPI:2-aminomethylpiperidine, AMHPI:2-(aminomethyl)homopiperidine, (2) those wherein $R^{16}$ is hydrogen and having a substituent in $R^{17}$, such as 2-(N-methylaminomethyl)pyrrolidine, 2-(N-ethylaminomethyl)pyrrolidine, 2-(N-n-propylaminomethyl)pyrrolidine, 2-(N-isopropylaminomethyl)pyrrolidine, 2-(N-methylaminomethyl)piperidine, 2-(N-ethylaminomethyl)piperidine, 2-(N-n-propylaminomethyl)piperidine, 2-(N-isopropylaminomethyl)piperidine, 2-(N-methylaminomethyl)homopiperidine, 2-(N-ethylaminomethyl)homopiperidine, 2-(N-n-propylaminomethyl)homopiperidine, 2-(N-isopropylaminomethyl)homopiperidine, (3) those wherein $R^{16}$ and $R^{17}$ are mutually bonded to form a hydrocarbon group, such as 1-(2-pyrrolidinylmethyl)pyrrolidine, 1-(2-piperidinylmethyl)pyrrolidine, 1-(2-homopiperidinylmethyl)pyrrolidine, (4) those wherein $R^{16}$ and $R^{17}$ are hydrogen and having one or more substituents in $R^{19}$ and $R^{20}$, such as 2-(1-aminoethyl)pyrrolidine, 2-(1-phenylaminomethyl)pyrrolidine, 2-(1-methyl-1-aminoethyl)pyrrolidine, 2-(1-phenyl-1-aminoethyl)pyrrolidine, 2-(1,1-diphenylaminomethyl)pyrrolidine, 2-(1-aminoethyl)piperidine, 2-(1-phenylaminomethyl)piperidine, 2-(1-methyl-1-aminoethyl)piperidine, 2-(1-phenyl-1-aminoethyl)piperidine, 2-(1,1-diphenylaminomethyl)piperidine, 2-(1-aminoethyl)homopiperidine, 2-(1-phenylaminomethyl)homopiperidine, 2-(1-methyl-1-aminoethyl)homopiperidine, 2-(1-phenyl-1-aminoethyl)homopiperidine, 2-(1,1-diphenylaminomethyl)homopiperidine, (5) those having a substituent in $R^{18}$, such as 2-(aminomethyl)-1-methylpyrrolidine, 2-(aminomethyl)-1-ethylpyrrolidine, 2-(aminomethyl)-1-n-propylpyrrolidine, 2-(aminomethyl)-1-isopropylpyrrolidine, 2-(aminomethyl)-1-methylpiperidine, 2-(aminomethyl)-1-ethylpiperidine, 2-(aminomethyl)-1-n-propylpiperidine, 2-(aminomethyl)-1-isopropylpiperidine, 2-(aminomethyl)-1-methylhomopiperidine, 2-(aminomethyl)-1-ethylhomopiperidine, 2-(aminomethyl)-1-n-propylhomopiperidine, 2-(aminomethyl)-1-isopropylhomopiperidine, (6) those having a substituent in $R^{21}$, such as 2-(aminomethyl)-3-methylpyrrolidine, 2-(aminomethyl)-4-methylpyrrolidine, 2-(aminomethyl)-5-methylpyrrolidine, 2-(aminomethyl)-3-ethylpyrrolidine, 2-(aminomethyl)-4-ethylpyrrolidine, 2-(aminomethyl)-5-ethylpyrrolidine, 2-(aminomethyl)-3-n-propylpyrrolidine, 2-(aminomethyl)-4-n-propylpyrrolidine, 2-(aminomethyl)-5-n-propylpyrrolidine, 2-(aminomethyl)-3-phenylpyrrolidine, 2-(aminomethyl)-4-phenylpyrrolidine, 2-(aminomethyl)-5-phenylpyrrolidine, 2-(aminomethyl)-3-methylpiperidine, 2-(aminomethyl)-4-methylpiperidine, 2-(aminomethyl)-5-methylpiperidine, 2-(aminomethyl)-6-methylpiperidine, 2-(aminomethyl)-3-ethylpiperidine, 2-(aminomethyl)-4-ethylpiperidine, 2-(aminomethyl)-5-ethylpiperidine, 2-(aminomethyl)-6-ethylpiperidine, 2-(aminomethyl)-3-n-propylpiperidine, 2-(aminomethyl)-4-n-propylpiperidine, 2-(aminomethyl)-5-n-propylpiperidine, 2-(aminomethyl)-6-n-propylpiperidine, 2-(aminomethyl)-3-phenylpiperidine, 2-(aminomethyl)-4-phenylpiperidine, 2-(aminomethyl)-5-phenylpiperidine, 2-(aminomethyl)-6-phenylpiperidine, 2-(aminomethyl)-3-methylhomopiperidine, 2-(aminomethyl)-4-methylhomopiperidine, 2-(aminomethyl)-5-methylhomopiperidine, 2-(aminomethyl)-6-methylhomopiperidine, 2-(aminomethyl)-7-methylhomopiperidine, 2-(aminomethyl)-3-ethylhomopiperidine, 2-(aminomethyl)-4-ethylhomopiperidine, 2-(aminomethyl)-5-ethylhomopiperidine, 2-(aminomethyl)-6-ethylhomopiperidine, 2-(aminomethyl)-7-ethylhomopiperidine, 2-(aminomethyl)-3-n-propylhomopiperidine, 2-(aminomethyl)-4-n-propylhomopiperidine, 2-(aminomethyl)-5-n-propylhomopiperidine, 2-(aminomethyl)-6-n-propylhomopiperidine, 2-(aminomethyl)-7-n-propylhomopiperidine, 2-(aminomethyl)-3-phenylhomopiperidine, 2-(aminomethyl)-4-phenylhomopiperidine, 2-(aminomethyl)-5-phenylhomopiperidine, 2-(aminomethyl)-6-phenylhomopiperidine, 2-(aminomethyl)-7-phenylhomopiperidine, (7) those wherein adjacent substituents in $R^{21}$ are bonded, such as 2-aminomethylindoline, 1-aminomethylisoindoline, 3-aminomethylisoindoline; as well as 2-aminomethylindoline derivatives, 1-aminomethylisoindoline derivatives and 3-aminomethylisoindoline derivatives in which substituents $R^{16}$, $R^{17}$, $R^{18}$, $R^{19}$ and $R^{20}$ are replaced by a hydrogen atom, a saturated or unsaturated, aliphatic or alicyclic hydrocarbon group, a monocyclic or polycyclic, aromatic or araliphatic hydrocarbon group, or any species of these hydrocarbon groups having one or more substituents. Examples include 2-aminomethylindoline derivatives, 1-aminomethylisoindoline derivatives and 3-aminomethylisoindoline derivatives having a hydrogen atom, a hydrocarbon group such as alkyl, alkenyl, cycloalkyl, cycloalkenyl, phenyl, naphthyl or phenylalkyl, and said hydrocarbon group further having various acceptable substituents such as alkyl, alkenyl, cycloalkyl, aryl, alkoxy, ester, acyloxy, halogen atoms, nitro group and cyano group. In particular, 2-aminomethylpyrrolidine is preferred.

The optically active diamine compounds which can be used are not limited to the illustrated compounds such as 2-picolylamine derivatives, 2-aminomethylquinoline derivatives, 1-aminomethylisoquinoline derivatives, 3-aminomethylisoquinoline derivatives, 2-aminomethylpyrrolidine derivatives, 2-aminomethylpiperidine derivatives, 2-(aminomethyl)homopiperidine derivatives, 2-aminomethylindoline derivatives, 1-aminomethylisoindoline derivatives, and 3-aminomethylisoindoline derivatives.

Next, general formula (5) representing the ruthenium complex of the invention:

$$\text{RuXYA} \quad (5)$$

has an optically active diphosphine compound A represented by general formula (2):

and here, substituents X and Y, and the optically active diphosphine compound may be appropriately selected from that similar to those for general formula (1).

Furthermore, some of the optically active ruthenium complexes represented by general formula (5) contain one or more organic compounds which are a reagent. Here, the organic compounds denote coordinate organic solvents, and examples include aromatic hydrocarbon solvents such as toluene and xylene, aliphatic hydrocarbon solvents such as pentane and hexane, halogen-containing hydrocarbon solvents such as methylene chloride, ether type solvents such as ether and tetrahydrofuran, alcohol type solvents such as methanol, ethanol, 2-propanol, butanol and benzyl alcohol, ketone type solvents such as acetone, methyl ethyl ketone and cyclohexyl ketone, organic solvents containing a hetero atom such as acetonitrile, DMF, N-methylpyrrolidone, DMSO and triethylamine.

Furthermore, as a 3-quinuclidinones used in the hydrogenation reaction, the following substances can be used as a ketone substrate: (1) 3-quinuclidinones, (2) 3-quinuclidinone derivatives having a substituent at 2-position: 2-methyl-3-quinuclidinone, 2,2-dimethyl-3-quinuclidinone, 2-ethyl-3-quinuclidinone, 2,2-diethyl-3-quinuclidinone, 2-n-propyl-3-quinuclidinone, 2,2-di-n-propyl-3-quinuclidinone, 2-i-propyl-3-quinuclidinone, 2,2-di-i-propyl-3-quinuclidinone, 2-n-butyl-3-quinuclidinone, 2,2-di-n-butyl-3-quinuclidinone, 2-t-butyl-3-quinuclidinone, 2-benzyl-3-quinuclidinone, (3) 3-quinuclidinone derivatives having a substituent at 4-position: 4-methyl-3-quinuclidinone, 4,4-dimethyl-3-quinuclidinone, 4-ethyl-3-quinuclidinone, 4,4-diethyl-3-quinuclidinone, 4-n-propyl-3-quinuclidinone, 4,4-di-n-propyl-3-quinuclidinone, 4-i-propyl-3-quinuclidinone, 4,4-di-t-propyl-3-quinuclidinone, 4-n-butyl-3-quinuclidinone, 4,4-di-n-butyl-3-quinuclidinone, 4-t-butyl-3-quinuclidinone, 4-benzyl-3-quinuclidinone, (4) 3-quinuclidinone derivatives having a substituent at 5-position: 5-methyl-3-quinuclidinone, 5,5-dimethyl-3-quinuclidinone, 5-ethyl-3-quinuclidinone, 5,5-diethyl-3-quinuclidinone, 5-n-propyl-3-quinuclidinone, 5,5-di-n-propyl-3-quinuclidinone, 5-i-propyl-3-quinuclidinone, 5,5-di-i-propyl-3-quinuclidinone, 5-n-butyl-3-quinuclidinone, 5,5-di-n-butyl-3-quinuclidinone, 5-t-butyl-3-quinuclidinone, 5-benzyl-3-quinuclidinone, (5) 3-quinuclidinone derivatives having a substituent at 6-position: 6-methyl-3-quinuclidinone, 6,6-dimethyl-3-quinuclidinone, 6-ethyl-3-quinuclidinone, 6,6-diethyl-3-quinuclidinone, 6-n-propyl-3-quinuclidinone, 6,6-di-n-propyl-3-quinuclidinone, 6-i-propyl-3-quinuclidinone, 6,6-di-i-propyl-3-quinuclidinone, 6-n-butyl-3-quinuclidinone, 6,6-di-n-butyl-3-quinuclidinone, 6-t-butyl-3-quinuclidinone, 6-benzyl-3-quinuclidinone, (6) 3-quinuclidinone derivatives having a substituent at 7-position: 7-methyl-3-quinuclidinone, 7,7-dimethyl-3-quinuclidinone, 7-ethyl-3-quinuclidinone, 7,7-diethyl-3-quinuclidinone, 7-n-propyl-3-quinuclidinone, 7,7-di-n-propyl-3-quinuclidinone, 7-i-propyl-3-quinuclidinone, 7,7-di-i-propyl-3-quinuclidinone, 7-n-butyl-3-quinuclidinone, 7,7-di-n-butyl-3-quinuclidinone, 7-t-butyl-3-quinuclidinone, 7-benzyl-3-quinuclidinone, (7) 3-quinuclidinone derivatives having a substituent at 8-position: 8-methyl-3-quinuclidinone, 8,8-dimethyl-3-quinuclidinone, 8-ethyl-3-quinuclidinone, 8,8-diethyl-3-quinuclidinone, 8-n-propyl-3-quinuclidinone, 8,8-di-n-propyl-3-quinuclidinone, 8-i-propyl-3-quinuclidinone, 8,8-di-i-propyl-3-quinuclidinone, 8-n-butyl-3-quinuclidinone, 8,8-di-n-butyl-3-quinuclidinone, 8-t-butyl-3-quinuclidinone, 8-benzyl-3-quinuclidinone; in addition, as 2-4 substitutes, 3-quinuclidinone derivatives having 2 to 4 arbitrary substituents at the following positions: (8) 2- and 4-positions, (9) 2- and 5-positions, (10) 2- and 6-positions, (11) 2- and 7-positions, (12) 2- and 8-positions, (13) 4- and 5-positions, (14) 4- and 6-positions, (15) 4- and 7-positions, (16) 4- and 8-positions, (17) 5- and 6-positions, (18) 5- and 7-positions, (19) 5- and 8-positions, (20) 6- and 7-positions, (21) 6- and 8-positions, (22) 7- and 8-positions;

as 3-6 substitutes, 3-quinuclidinone derivatives having 3 to 6 arbitrary substituents at the following positions: (23) 2-, 4-, 5-positions, (24) 2-, 4-, 6-positions, (25) 2-, 4-, 7-positions, (26) 2-, 4-, 8-positions, (27) 2-, 5-, 6-positions, (28) 2-, 5-, 7-positions, (29) 2-, 5-, 8-positions, (30) 2-, 6-, 7-positions, (31) 2-, 6-, 8-positions, (32) 2-, 7-, 8-positions, (33) 4-, 5-, 6-positions, (34) 4-, 5-, 7-positions, (35) 4-, 5-, 8-positions, (36) 5-, 6-, 7-positions, (37) 5-, 6-, 8-positions, (38) 6-, 7-, 8-positions;

as 4-8 substitutes, 3-quinuclidinone derivatives having 4 to 8 arbitrary substituents at the following positions: (39) 2-, 4-, 5-, 6-positions, (40) 2-, 4-, 5-, 7-positions, (41) 2-, 4-, 5-, 8-positions, (42) 2-, 4-, 6-, 7-positions, (43) 2-, 4-, 6-, 8-positions, (44) 2-, 5-, 6-, 7-positions, (45) 2-, 5-, 6-, 8-positions, (46) 2-, 6-, 7-, 8-positions, (47) 4-, 5-, 6-, 7-positions, (48) 4-, 5-, 6-, 8-positions, (49) 5-, 6-, 7-, 8-positions;

as 5-10 substitutes, 3-quinuclidinone derivatives having 5 to 10 arbitrary substituents at the following positions: (50) 2-, 4-, 5-, 6-, 7-positions, (51) 2-, 4-, 5-, 6-, 8-positions, (52) 2-, 4-, 6-, 7-, 8-positions, (53) 2-, 5-, 6-, 7-, 8-positions, (54) 4-, 5-, 6-, 7-, 8-positions;

as 6-11 substitutes, 3-quinuclidinone derivatives having 6 to 11 arbitrary substituents including alkyl groups with a carbon number of 1-10 or cyclic hydrocarbon groups which may have one or more substituents, at (55) 2-, 4-, 5-, 6-, 7-, 8-positions.

The ruthenium complex of general formula (1) can be synthesized by reacting an optically active ruthenium complex of general formula (5) with a diamine compound or an optically active diamine compound. The optically active ruthenium complex of general formula (5) can be synthesized by reacting an optically active diphosphine compound with a ruthenium complex which is a raw material.

As a ruthenium complex which is a starting material for the synthesis of complexes, ruthenium complexes of zero valency, monovalency, divalency, trivalency and a higher valency can be used. In case of using zero-valent or monovalent ruthenium complexes, oxidation of the ruthenium is necessary before the final step. In case of using divalent ruthenium complexes, the synthesis can be carried out by reacting the ruthenium complex with an optically active diphosphine compound, and with a diamine compound or an optically active diamine compound in this sequence, or in the reverse sequence, or simultaneously. In case of using trivalent, tetravalent or higher-valent ruthenium complexes as a starting material, reduction of the ruthenium is necessary before the final step.

As ruthenium complexes used as a starting material, inorganic ruthenium compounds such as ruthenium chloride (III) hydrate, ruthenium bromide (III) hydrate and ruthenium iodide (III) hydrate; ruthenium compounds coordinated with diene such as a [ruthenium dichloride (norbornadiene)] polynuclear complex, a [ruthenium dichloride (cycloocta-1,5-diene)] polynuclear complex and bis(methylallyl)ruthenium (cycloocta-1,5-diene); ruthenium complexes coordinated with an aromatic compound such as a [ruthenium dichloride (benzene)] dinuclear complex, a [ruthenium dichloride (p-cymene)] dinuclear complex, a [ruthenium dichloride (trimethylbenzene)] dinuclear complex and a [ruthenium dichloride (hexamethylbenzene)] dinuclear complex; and complexes coordinated with a phosphine compound such as dichlorotris(triphenylphosphine)ruthenium are used. Additionally, any ruthenium complexes having a ligand replaceable with an optically active diphosphine compound, a diamine compound or an optically active diamine compound may be used without limitation to those described above. For example, a variety of ruthenium complexes shown in COMPREHENSIVE ORGANOMETALLIC CHEMISTRY II Vol. 7, p. 294-296 (PERGAMON) can be used as a starting material.

In case of using trivalent ruthenium complexes as a starting material, for example, a phosphine-ruthenium halide complex can be synthesized by reacting ruthenium halide (III) with an excess of a phosphine compound. Subsequently, by reacting the obtained phosphine-ruthenium halide complex with an amine compound, the amine-phosphine-ruthenium halide complex desired can be obtained.

Namely, by reacting $RuCl_2(PPh_3)_3$ in benzene with ethylenediamine, $RuCl_2(PPh_3)_2(en)$ is obtained. However, with this method, the reaction is in an inhomogeneous system, and there is a tendency that unreacted raw materials remain. In the meantime, in case of changing the reaction solvent to a solvent such as methylene chloride or chloroform, the reaction can be carried out in a homogeneous condition, so that operability can be improved.

The reaction of a ruthenium halide with a phosphine compound is carried out in an aromatic hydrocarbon solvent such as toluene or xylene, an aliphatic hydrocarbon solvent such as pentane or hexane, a halogen-containing hydrocarbon solvent such as methylenechloride, an ether type solvent such as ether or tetrahydrofuran, an alcohol type solvent such as methanol, ethanol, 2-propanol, butanol or benzyl alcohol, an organic solvent containing a hetero atom such as acetonitrile, DMF, N-methylpyrrolidone or DMSO, at a reaction temperature between −100° C. and 200° C., to obtain a phosphine-ruthenium halide complex.

The reaction of the obtained phosphine-ruthenium halide complex with an amine compound is carried out in an aromatic hydrocarbon solvent such as toluene or xylene, an aliphatic hydrocarbon solvent such as pentane or hexane, a halogen-containing hydrocarbon solvent such as methylenechloride, an ether type solvent such as ether or tetrahydrofuran, an alcohol type solvent such as methanol, ethanol, 2-propanol, butanol or benzyl alcohol, an organic solvent containing a hetero atom such as acetonitrile, DMF, N-methylpyrrolidone or DMSO, at a reaction temperature between −100° C. and 200° C., to obtain an amine-phosphine-ruthenium halide complex.

In the meantime, it is also possible to use the following reaction method: using a divalent ruthenium complex from the beginning, this complex is reacted with a phosphine compound and an amine compound in this sequence, or in the reverse sequence, or simultaneously. As an example, a ruthenium compound coordinated with diene such as a [ruthenium dichloride(norbornadiene)] polynuclear complex, a [ruthenium dichloride (cycloocta-1,5-diene)] polynuclear complex or bis(methylallyl)ruthenium(cyclooctadiene); or a ruthenium complex coordinated with an aromatic compound such as a [ruthenium dichloride (benzene)] dinuclear complex, a [ruthenium dichloride (p-cymene)] dinuclear complex, a [ruthenium dichloride (trimethylbenzene)] dinuclear complex or a [ruthenium dichloride (hexamethylbenzene)] dinuclear complex; or a complex coordinated with a phosphine compound such as dichlorotris(triphenylphosphine)ruthenium is reacted with a phosphine compound in an aromatic hydrocarbon solvent such as toluene or xylene, an aliphatic hydrocarbon solvent such as pentane or hexane, a halogen-containing hydrocarbon solvent such as methylenechloride, an ether type solvent such as ether or tetrahydrofuran, an alcohol type solvent such as methanol, ethanol, 2-propanol, butanol or benzyl alcohol, an organic solvent containing a hetero atom such as acetonitrile, DMF, N-methylpyrrolidone or DMSO, at a reaction temperature between −100° C. and 200° C., to obtain a phosphine-ruthenium halide complex.

The reaction of the obtained phosphine-ruthenium halide complex with an amine compound is carried out in an aromatic hydrocarbon solvent such as toluene or xylene, an aliphatic hydrocarbon solvent such as pentane or hexane, a halogen-containing hydrocarbon solvent such as methylenechloride, an ether type solvent such as ether or tetrahydrofuran, an alcohol type solvent such as methanol, ethanol, 2-propanol, butanol or benzyl alcohol, an organic solvent containing a hetero atom such as acetonitrile, DMF, N-methylpyrrolidone or DMSO, at a reaction temperature between −100° C. and 200° C., to obtain an amine-phosphine-ruthenium complex. In addition, in a similar condition, a cationic ruthenium complex such as [chlororuthenium(BINAP)(benzene)]chloride is reacted with an amine compound to obtain an amine-phosphine-ruthenium halide complex.

Moreover, by reducing the obtained amine-phosphine-ruthenium halide complex using a boron hydride salt, a ruthenium hydride complex can be obtained. For example, the amine-phosphine-ruthenium halide complex is reacted with a hydrogenated boron metal salt such as sodium borohydride or potassium borohydride in an aromatic hydrocarbon solvent such as toluene or xylene, an aliphatic hydrocarbon solvent such as pentane or hexane, a halogen-containing hydrocarbon solvent such as methylenechloride, an ether type solvent such as ether or tetrahydrofuran, an alcohol type solvent such as methanol, ethanol, 2-propanol, butanol or benzyl alcohol, an organic solvent containing a hetero atom such as acetonitrile, DMA, DMF, N-methylpyrrolidone or DMSO, at a reaction temperature between −100° C. and 200° C., to obtain an ruthenium hydride complex. In addition, first a phosphine ruthenium halide complex is converted to a phosphine-ruthenium hydride complex, which is then reacted with an amine compound to obtain a ruthenium hydride complex.

For example, in case of using the ruthenium complex synthesized as above represented by general formula (1) or (5) as a hydrogenation catalyst, its amount of use varies depending on the type of reaction vessel and economic efficiency; however, it should be 1/100 to 1/10,000,000 relative to the 3-quinuclidinones which is a reaction substrate, and preferably 1/500 to 1/1,000,000.

An optically active ruthenium complex of general formula (1) in which X is hydrogen and Y is a tetrahydroborate anion or a tetrafluoroborate anion is mixed with a 3-quinuclidinones without addition of a base, and the mixture is stirred under hydrogen pressure or under the presence of a hydrogen-donating material. By this, the 3-quinuclidinones can be hydrogenated. In case of using an excess of 3-quinuclidinones relative to the catalyst, it may be desirable to add a base. In the meantime, in case that X or Y is a group other than hydrogen, it is also effective to hydrogenate 3-quinuclidinones by mixing the optically active ruthenium complex with 3-quinuclidinones under the presence of a base, then stirring the mixture under hydrogen pressure or under the presence of a hydrogen-donating material.

An optically active ruthenium complex of general formula (5) in which X is hydrogen and Y is a tetrahydroborate anion or a tetrafluoroborate anion is added with a diamine compound or an optically active diamine compound represented by general formula (3) or (4) without addition of a base, then mixed with a carbonyl compound, and the mixture is stirred under hydrogen pressure or under the presence of a hydrogen-donating material. By this, 3-quinuclidinones can be hydrogenated. In case of using an excess of 3-quinuclidinones relative to the catalyst, it may be desirable to add a base. In the meantime, in case that X or Y is a group other than hydrogen, it is also effective to hydrogenate 3-quinuclidinones by mixing the optically active ruthenium complex with 3-quinuclidinone after the addition of a base and a diamine compound or an optically active diamine compound represented by general formula (3) or (4), then stirring the mixture under hydrogen pressure or under the presence of a hydrogen-donating material.

The amount of a diamine compound or an optically active diamine ligand used here is 0.5-2.5 equivalents, preferably 1-2 equivalents, relative to the amount of the ruthenium complex of general formula (5).

In addition, as to a base used in the invention, alkali metal salts such as KOH, $KOCH_3$, $KOCH(CH_3)_2$, $KOC(CH_3)_3$, $KC_{10}H_8$, LiOH, $LiOCH_3$, $LiOCH(CH_3)_2$ and $LiOC(CH_3)_3$, alkaline earth metal salts, or quaternary ammonium salts are used. The amount of a base added is an amount achieving the base concentration of 0.001-0.1, preferably 0.01-0.05.

Further, the hydrogen-donating material means a lower alcohol such as methanol, ethanol, n-propanol, isopropanol or butanol, and formic acid; ethanol or a mixture of ethanol with other lower alcohol is preferred.

As a solvent, any solvents which can solubilize reaction materials and catalysts can be used. Examples which can be used are: aromatic hydrocarbon solvents such as toluene and xylene, aliphatic hydrocarbon solvents such as pentane and hexane, halogen-containing hydrocarbon solvents such as methylenechloride, ether type solvents such as ether and tetrahydrofuran, alcohol type solvents such as methanol, ethanol, n-propanol, 2-propanol, butanol and benzyl alcohol, organic solvents containing a hetero atom such as acetonitrile, DMF, N-methylpyrrolidone and DMSO. Since reaction products are alcohol compounds, alcohol type solvents are more preferable. When a reaction substrate is hardly soluble in a solvent, a mixture solvent made by selecting the above solvents can be used.

The amount of a solvent in the preparation of optically active quinuclidinols is determined on the basis of solubility of a reaction substrate and economic efficiency. For example, in case of ethanol, the substrate concentration is preferably 20-50 wt %, although from 1% or less to almost no solvent concentration may be applied for the reaction depending on the substrate.

In addition, while a hydrogen pressure of 1 atm is enough in the preparation of optically active quinuclidinols of the invention owing to the extremely high activity of the present catalyst system, the range of 1-200 atm, preferably 3-100 atm is desirable considering economic efficiency; however, high activities can also be maintained at 50 atm or less considering the economic efficiency of an entire process.

As to the reaction temperature in the preparation of optically active quinuclidinols, reaction is carried out preferably at −30° C. to 100° C., and more preferably at 0° C. to 80° C. Considering economic efficiency, the range from 20° C. to 50° C. is most preferred. In the present invention, one of the characteristics is that reactions can take place even at a low temperature of −30° C. to 0° C. Reaction time varies depending on reaction conditions such as a concentration of reaction substrate, temperature and pressure; however, a reaction is completed within several minutes to several tens of hours. Examples are illustrated specifically.

Meanwhile, optically active diphosphine compounds in the optically active ruthenium complexes of general formulae (1) and (5) can be obtained as either (+)-forms or (−)-forms, though the indication is omitted here. In addition, by selecting either of these (+)-form and (−)-form, the optically active 3-quinuclidinols with a desirable absolute configuration can be obtained. Furthermore, a combination of the absolute configuration of a diphosphine compound in an optically active ruthenium complex of general formula (1) and the absolute configuration of an optically active diamine compound, and a combination of the absolute configuration of a diphosphine compound in an optically active ruthenium complex of general formula (5) and the absolute configuration of an optically active diamine compound added, are important to obtain high optical yields.

EXAMPLES

Hydrogenation of carbonyl compounds in the invention can be carried out in a batch type reaction or in a continuous type reaction. Hereinafter, the invention is explained in detail showing examples. However, the invention is not limited to the following examples. Meanwhile, in the below examples all reactions were carried out under an inactive gas atmosphere such as argon gas or nitrogen gas. In addition, as to solvent used in the reaction, those which had been dried and degassed were used. Hydrogenation of 3-quinuclidinone was carried out in an autoclave under hydrogen pressure.

The equipments listed below were used in the following measurements.

NMR: LA400-type apparatus (400 MHz)
(Manufactured by Nihon Denshi Co., Ltd.)
Internal standard: $^1$H-NMR Tetramethylsilane
External standard: $^{31}$P-NMR 85% Phosphoric acid
Optical purity: Gas chromatography
Chirasil-DEX CB (0.25 mm×25 m, DF=0.25 μm)
(Manufactured by CHROMPACK Co., Ltd.)
BETA DEX 120 (0.25 mm×30 m, DF=0.25 μm)
(Manufactured by SUPELCO)

Example 1

Synthesis of RuBr$_2$-[(S,S)-xylskewphos](pica)

(1) Synthesis of Ru[(S,S)-xylskewphos](methylallyl)$_2$ (S,S)-XylSKEWPHOS (110 mg, 0.2 mmol) and Ru(cycloocta-1,5-diene)(methylallyl)$_2$ (64 mg, 0.2 mmol) were placed in a 50-mL Schlenk tube replaced with argon. Then, hexane 5 mL was added and the mixture was stirred at 70° C. for 6 h. The insoluble material was filtered by a glass filter, and the solvent was distilled off.

(2) Synthesis of RuBr$_2$-[(S,S)-xylskewphos]

Under an argon atmosphere, the Ru[(S,S)-xylskewphos](methylallyl)$_2$ complex (153 mg, 0.2 mmol) synthesized in (1) was dissolved in 15 mL of acetone, added with 47%-HBr methanolic solution (0.046 mL, 0.4 mmol), degassed and stirred at room temperature for 30 min. After distillation of the solvent, the residue was used for the subsequent reaction without purification.

(3) Synthesis of RuBr$_2$-[(S,S)-xylskewphos](pica)

Under an argon atmosphere, 2-picolylamine (21.6 mg, 0.2 mmol) was placed in the RuBr$_2$-[(S,S)-xylskewphos] complex (163 mg, 0.2 mmol) synthesized in (2). Then, dimethylformamide (5 mL) was added and the mixture was degassed and stirred at room temperature for 1 night. The reaction solution was filtered through a glass filter filled with silica gel, then the solvent was distilled off to obtain 178 mg of RuBr$_2$-[(S,S)-xylskewphos](pica) (97% yield).
$^{31}$P-NMR spectrum (161.7 MHz, C$_6$D$_6$): δ62.4 (d, J=42 Hz), 43.5 (d, J=43 Hz).

Example 2

Synthesis of RuCl$_2$-[(S,S)-3,5-diEtskewphos](pica)

(S,S)-3,5-diEtSKEWPHOS (56 mg, 0.084 mmol) and [RuCl$_2$(p-cymene)] (26 mg, 0.043 mmol) were placed in a 50-mL Schlenk tube replaced with argon. Then, dimethylformamide (3 mL) was added and the mixture was degassed and stirred for 5.5 h while being heated at 100° C. Then, 2-picolylamine (9.1 mg, 0.084 mmol) was added and the mixture was degassed and stirred at room temperature for 16 h. The solvent was distilled off to obtain 76 mg of RuCl$_2$-[(S,S)-3,5-diEtskewphos](pica) (95% yield).
$^{31}$P-NMR spectrum (161.7 MHz, C$_6$D$_6$): δ40.09 (d, J=58 Hz), 31.76 (d, J=58 Hz).

Example 3

Synthesis of RuBr$_2$-[(S,S)-tolskewphos](pica)

Synthesis was carried out similar to the Example 1, except that TolSKEWPHOS was used as the diphosphine compound in place of XylSKEWPHOS, and 129 mg of RuBr$_2$-[(S,S)-tolskewphos](pica) (95% yield) was obtained.
$^{31}$P-NMR spectrum (161.7 MHz, C$_6$D$_6$): δ63.0 (d, J=43 Hz), 44.1 (d, J=45 Hz).

Example 4

Synthesis of RuBr$_2$-[(S,S)-4-t-Buskewphos](pica)

Synthesis was carried out similar to the Example 1, except that 4-t-BuSKEWPHOS was used as the diphosphine compound in place of XylSKEWPHOS, and 18 mg of RuBr$_2$-[(S,S)-4-t-Buskewphos](pica) (90% yield) was obtained.
$^{31}$P-NMR spectrum (161.7 MHz, C$_6$D$_6$): major: δ38.7 (d, J=61 Hz), 29.1 (d, J=61 Hz), minor: δ63.4 (d, J=45 Hz), 58.5 (d, J=43 Hz), 44.3 (d, J=33 Hz), 44.0 (d, J=33 Hz).

Example 5

Synthesis of RuBr$_2$-[(S,S)-skewphos](pica)

Synthesis was carried out similar to the Example 1, except that SKEWPHOS was used as the diphosphine compound in place of XylSKEWPHOS, and 301 mg of RuBr$_2$-[(S,S)-skewphos](pica) (93% yield) was obtained.
$^{31}$P-NMR spectrum (161.7 MHz, C$_6$D$_6$): major: δ64.5 (d, J=43 Hz), 45.4 (d, J=45 Hz), minor: δ60.6 (d, J=49 Hz), 46.3 (d, J=51 Hz).

Example 6

Synthesis of RuBr$_2$-[(S,S)-xylskewphos](6-Me-pica)

Synthesis was carried out similar to the Example 1, except that 2-(aminomethyl)-6-methylpyridine was used as the diamine compound in place of 2-picolylamine, and 128 mg of RuBr$_2$-[(S,S)-xylskewphos] (6-Me-pica) (83% yield) was obtained.

Example 7

Synthesis of RuCl$_2$-[(S,S)-xylskewphos](bnpica)

(S,S)-XylSKEWPHOS (48 mg, 0.087 mmol) and [RuCl$_2$(p-cymene)]$_2$ (27 mg, 0.045 mmol) were placed in a 50-mL Schlenk tube replaced with argon. Then, dimethylformamide (3 mL) was added and the mixture was degassed and stirred for 5.5 h while being heated at 100° C. Then, a methylene chloride solution (2 mL) of 2-(N-benzylaminomethyl)pyridine (17.2 mg, 0.087 mmol) was added and the mixture was degassed and stirred at room temperature for 16 h. The solvent was distilled off to obtain 76 mg of RuCl$_2$-[(S,S)-xylskewphos](bnpica) (95% yield).
$^{31}$P-NMR spectrum (161.7 MHz, C$_6$D$_6$): δ39.9 (d, J=61 Hz), 30.4 (d, J=58 Hz).

Example 8

Synthesis of RuBr$_2$-[(S,S)-xylskewphos](amq)

Synthesis was carried out similar to the Example 1, except that 2-aminomethylquinoline was used as the diamine compound in place of 2-picolylamine, and 100 mg of RuBr$_2$-[(S,S)-xylskewphos](amq) (90% yield) was obtained.

Example 9

RuBr$_2$-[(S,S)-xylskewphos](pica) (1.8 mg, 0.002 mmol), 3-quinuclidinone (0.25 g, 2 mmol), KOC(CH$_3$)$_3$ (9 mg, 0.08 mmol) were placed in a 100-mL glass autoclave, replaced with argon, subsequently added with ethanol (4 mL), degassed and replaced with argon. Hydrogen was introduced until the pressure became 10 atm at 30° C., and the reaction was started. After the reaction solution was stirred for 19 h, the reaction pressure was decreased to a normal pressure, and the quantity and optical purity of the product 3-quinuclidinol were determined by gas chromatography of the reaction solution; the result showed that (R)-3-quinuclidinol with 84% ee was formed with a yield of 92%.

Example 10

Hydrogenation of 3-quinuclidinone was carried out similar to the Example 9 except that 2-propanol was used as the solvent in place of ethanol, and (R)-3-quinuclidinol with 78% ee was formed with a yield of 99%.

Example 11

Hydrogenation of 3-quinuclidinone was carried out similar to the Example 9 except that $RuCl_2$-[(S,S)-3,5-diEtskewphos] (pica) was used as the catalyst in place of $RuBr_2$-[(S,S)-xylskewphos] (pica), and (R)-3-quinuclidinol with 81% ee was formed with a yield of 94%.

Example 12

Hydrogenation of 3-quinuclidinone was carried out similar to the Example 9 except that $RuBr_2$[(S,S)-tolskewphos] (pica) was used as the catalyst in place of $RuBr_2$-[(S,S)-xylskewphos] (pica), and (R)-3-quinuclidinol with 78% ee was formed with a yield of 72%.

Example 13

Hydrogenation of 3-quinuclidinone was carried out similar to the Example 9 except that $RuBr_2$-[(S,S)-4-t-Buskewphos] (pica) was used as the catalyst in place of $RuBr_2$-[(S,S)-xylskewphos](pica), and (R)-3-quinuclidinol with 57% ee was formed with a yield of 96%.

Example 14

Hydrogenation of 3-quinuclidinone was carried out similar to the Example 9 except that $RuBr_2$-[(S,S)-skewphos] (pica) was used as the catalyst in place of $RuBr_2$-[(S,S)-xylskewphos] (pica), and (R)-3-quinuclidinol with 72% ee was formed with a yield of 92%.

Example 15

Hydrogenation of 3-quinuclidinone was carried out similar to the Example 9 except that $RuBr_2$-[(S,S)-xylskewphos](6-Me-pica) was used as the catalyst in place of $RuBr_2$-[(S,S)-xylskewphos](pica), and (R)-3-quinuclidinol with 82% ee was formed with a yield of 95%.

Example 16

Hydrogenation of 3-quinuclidinone was carried out similar to the Example 9 except that $RuCl_2$-[(S,S)-xylskewphos](bn-pica) was used as the catalyst in place of $RuBr_2$-[(S,S)-xylskewphos](pica), and (R)-3-quinuclidinol with 66% ee was formed with a yield of 90%.

Example 17

$RuBr_2$-[(S,S)-xylskewphos](pica) (0.5 mg, 0.54 μmol), 3-quinuclidinone (20.37 g, 162.7 mmol), $KOC(CH_3)_3$ (219 mg, 1.9 mmol) were placed in a 500-mL glass autoclave, replaced with argon, subsequently added with ethanol (65 mL), degassed and replaced with argon. Hydrogen was introduced until the pressure became 10 atm at 30° C., and the reaction was started. After the reaction solution was stirred for 19 h, the reaction pressure was decreased to a normal pressure, and the quantity and optical purity of the product 3-quinuclidinol were determined by gas chromatography of the reaction solution; the result showed that (R)-3-quinuclidinol with 89% ee was formed with a yield of 98%.

Example 18

Hydrogenation of 3-quinuclidinone was carried out similar to the Example 17 except that the amount of $KOC(CH_3)_3$ was reduced from 219 mg (1.9 mmol) to 146 mg (1.3 mmol), and (R)-3-quinuclidinol with 89% ee was formed with a yield of 59%.

TABLE 1

|  | Ru complex | Substrate/Ru complex/base | $H_2$ (atm) | Solvent | Temperature (° C.) | Time (h) | Yield (%) | ee(%) |
|---|---|---|---|---|---|---|---|---|
| Example 9 | (S,S)-XylSKEWPHOS PICA | 1000/1/40 | 10 | EtOH | 30 | 19 | 92 | 84 (R) |
| Example 10 | (S,S)-XylSKEWPHOS PICA | 1000/1/40 | 10 | 2-propanol | 30 | 19 | 99 | 78 (R) |
| Example 11 | (S,S)-3,5-diEtSKEWPHOS PICA | 1000/1/40 | 10 | EtOH | 30 | 19 | 94 | 81 (R) |
| Example 12 | (S,S)-TolSKEWPHOS PICA | 1000/1/40 | 10 | EtOH | 30 | 19 | 72 | 78 (R) |
| Example 13 | (S,S)-4-tBuSKEWPHOS PICA | 1000/1/40 | 10 | EtOH | 30 | 19 | 96 | 57 (R) |
| Example 14 | (S,S)-SKEWPHOS PICA | 1000/1/40 | 10 | EtOH | 30 | 19 | 92 | 72 (R) |
| Example 15 | (S,S)-XylSKEWPHOS 6-Me-PICA | 1000/1/40 | 10 | EtOH | 30 | 19 | 95 | 82 (R) |
| Example 16 | (S,S)-XylSKEWPHOS BnPICA | 1000/1/40 | 10 | EtOH | 30 | 19 | 90 | 66 (R) |
| Example 17 | (S,S)-XylSKEWPHOS PICA | 300000/1/3600 | 10 | EtOH | 30 | 19 | 96 | 89 (R) |

TABLE 1-continued

| | Ru complex | Substrate/ Ru complex/base | H₂ (atm) | Solvent | Temperature (° C.) | Time (h) | Yield (%) | ee(%) |
|---|---|---|---|---|---|---|---|---|
| Example 18 | (S,S)-XylSKEWPHOS PICA | 300000/1/2400 | 10 | EtOH | 30 | 19 | 59 | 89 (R) |

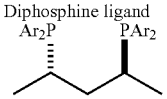

Diphosphine ligand

Ar₂P  PAr₂

Ar = C₆H₅     (S,S)-SKEWPHOS
4-CH₃C₆H₄     (S,S)-TolSKEWPHOS
4-C(CH₃)₃C₆H₄     (S,S)-4-t-BuSKEWPHOS
3,5-(CH₃)₂C₆H₃     (S,S)-XylSKEWPHOS
3,5-(C₂H₅)₂C₆H₃     (S,S)-3,5-dIEtSKEWPHOS

Amin ligand

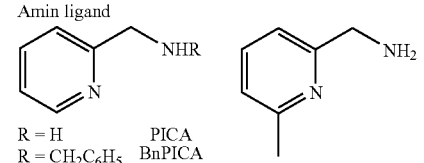

R = H    PICA
R = CH₂C₆H₅    BnPICA

6-Me-PICA

Example 19

Synthesis of RuCl₂-[(R,R)-xylskewphos][(S)-ampy]

(R,R)-XylSKEWPHOS (41 mg, 0.074 mmol) and [RuCl₂(p-cymene)]₂ (23 mg, 0.037 mmol) were placed in a 50-mL Schlenk tube replaced with argon. Then, dimethylformamide (5 mL) was added and the mixture was degassed and stirred for 7 h while being heated at 100° C. Then, (S)-2-aminomethylpyrrolidine (7.4 mg, 0.074 mmol) was added and the mixture was degassed and stirred at room temperature for 6 h. The solvent was distilled off to obtain 55 mg of RuCl₂-[(R,R)-xylskewphos][(S)-ampy] (90% yield).

$^{31}$P-NMR spectrum (161.7 MHz, $C_6D_6$): δ60.5 (d, J=49 Hz), 43.9 (d, J=49 Hz), 39.8 (d, J=61 Hz), 30.2 (d, J=61 Hz).

Example 20

Synthesis of RuCl₂-[(S,S)-xylskewphos][(S)-ampy]

(S,S)-XylSKEWPHOS (41 mg, 0.074 mmol) and [RuCl₂(p-cymene)]₂ (23 mg, 0.037 mmol) were placed in a 50-mL Schlenk tube replaced with argon. Then, dimethylformamide (5 mL) was added and the mixture was degassed and stirred for 7 h while being heated at 100° C. Then, (S)-2-aminomethylpyrrolidine (7.4 mg, 0.074 mmol) was added and the mixture was degassed and stirred at room temperature. The solvent was distilled off to obtain 52 mg of RuCl₂-[(S,S)-xylskewphos][(S)-ampy] (85% yield).

$^{31}$P-NMR spectrum (161.7 MHz, $C_6D_6$): δ39.8 (d, J=61 Hz), 30.2 (d, J=61 Hz).

Example 21

Synthesis of RuCl₂-[(S,S)-xylskewphos][(R)-ampy]

Synthesis was carried out similar to the Example 20, except that (R)-2-(aminomethyl)-1-ethylpyrrolidine was used as the diamine compound in place of (S)-2-aminomethylpyrrolidine, and 50 mg of RuCl₂-[(S,S)-xylskewphos][(R)-ampy] (80% yield) was obtained.

$^{31}$P-NMR spectrum (161.7 MHz, $C_6D_6$): δ39.8 (d, J=59 Hz), 30.3 (d, J=61 Hz).

Example 22

Synthesis of RuCl₂-[(R,R)-xylskewphos][(R)-amepy]

Synthesis was carried out similar to the Example 19, except that (R)-2-(aminomethyl)-1-ethylpyrrolidine was used as the diamine compound in place of (S)-2-aminomethylpyrrolidine, and 52 mg of RuCl₂-[(R,R)-xylskewphos][(R)-amepy] (83% yield) was obtained.

$^{31}$P-NMR spectrum (161.7 MHz, $C_6D_6$): δ65.1 (d, J=43 Hz), 47.8 (d, J=45 Hz), 39.8 (d, J=59 Hz), 30.3 (d, J=61 Hz).

Example 23

Synthesis of RuCl₂-[(R,R)-xylskewphos][(S)-pmpy]

(R,R)-XylSKEWPHOS (22 mg, 0.040 mol) and [RuCl₂(p-cymene)]₂ (13 mg, 0.020 mmol) were placed in a 50-mL Schlenk tube replaced with argon. Then, dimethylformamide (3 mL) was added and the mixture was degassed and stirred for 4 h while being heated at 100° C. Then, (S)-1-(2-pyrrolidinylmethyl)pyrrolidine (6.1 mg, 0.040 mmol) was added and the mixture was degassed and stirred at room temperature for 12 h. The solvent was distilled off to obtain 33 mg of RuCl₂-[(R,R)-xylskewphos][(S)-pmpy] (95% yield).

$^{31}$P-NMR spectrum (161.7 MHz, $C_6D_6$): δ52.8 (d, J=49 Hz), 39.8 (d, J=58 Hz), δ32.7 (d, J=49 Hz), 30.3 (d, J=58 Hz).

Example 24

Synthesis of RuCl₂-[(S,S)-xylskewphos][(S)-pmpy]

(S,S)-XylSKEWPHOS (43 mg, 0.078 mmol) and [RuCl₂(p-cymene)]₂ (24 mg, 0.040 mmol) were placed in a 50-mL Schlenk tube replaced with argon. Then, dimethylformamide (3 mL) was added and the mixture was degassed and stirred for 4 h while being heated at 100° C. Then, (S)-1-(2-pyrrolidinylmethyl)pyrrolidine (12 mg, 0.078 mmol) was added and the mixture was degassed and stirred at room temperature for 12 h. The solvent was distilled off to obtain 61 mg of RuCl₂-[(S,S)-xylskewphos][(S)-pmpy] (90% yield).

$^{31}$P-NMR spectrum (161.7 MHz, $C_6D_6$): δ45.1 (d, J=49 Hz), 40.9 (d, J=47 Hz), 39.8 (d, J=60 Hz), 30.2 (d, J=61 Hz).

Example 25

RuCl₂-[(R,R)-xylskewphos][(S)-ampy] (1.6 mg, 0.002 mmol), 3-quinuclidinone (0.25 g, 2 mmol), KOC(CH₃)₃ (9 mg, 0.08 mmol) were placed in a 100-mL glass autoclave, replaced with argon, subsequently added with ethanol (4 mL), degassed and replaced with argon. Hydrogen was introduced until the pressure became 10 atm at 30° C., and the reaction was started. After the reaction solution was stirred for 19 h, the reaction pressure was decreased to a normal pressure, and the quantity and optical purity of the product 3-quinuclidinol were determined by gas chromatography of the reaction solution; the result showed that (S)-3-quinuclidinol with 86% ee was formed with a yield of 96%.

Example 26

Hydrogenation of 3-quinuclidinone was carried out similar to the Example 25 except that 2-propanol was used as the solvent in place of ethanol, and (S)-3-quinuclidinol with 66% ee was formed with a yield of 99%.

Example 27

Hydrogenation of 3-quinuclidinone was carried out similar to the Example 25 except that ethanol:t-butanol=3:1 was used as the solvent in place of ethanol, and (S)-3-quinuclidinol with 86% ee was formed with a yield of 95%.

Example 28

$RuCl_2$-[(R,R)-xylskewphos][(S)-ampy] (3.3 mg, 0.004 mmol), 3-quinuclidinone (0.25 g, 2 mmol), $KOC(CH_3)_3$ (18 mg, 0.16 mmol) were placed in a 100-mL glass autoclave, replaced with argon, subsequently added with ethanol (4 mL), degassed and replaced with argon. Hydrogen was introduced until the pressure became 10 atm at 0° C., and the reaction was started. After the reaction solution was stirred for 19 h, the reaction pressure was decreased to a normal pressure, and the quantity and optical purity of the product 3-quinuclidinol were determined by gas chromatography of the reaction solution; the result showed that (S)-3-quinuclidinol with 88% ee was formed with a yield of 89%.

Example 29

Hydrogenation of 3-quinuclidinone was carried out similar to the Example 25 except that $RuCl_2$-[(S,S)-xylskewphos][(R)-ampy] was used as the catalyst in place of $RuCl_2$-[(R,R)-xylskewphos][(S)-ampy], and (R)-3-quinuclidinol with 65% ee was formed with a yield of 89%.

Comparative Example 1

Hydrogenation of 3-quinuclidinone was carried out similar to the Example 9 in which the synthesis was carried out by the method described in JP (A) No. 11-289600, except that $RuCl_2$-[(S,S)-xylskewphos] [(S)-daipen] synthesized by the method described in JP (A) No. 2003-252884 was used as the catalyst in place of $RuBr_2$-[(S,S)-xylskewphos](pica), and (R)-3-quinuclidinol with 38% ee was formed with a yield of 50%.

Comparative Example 2

$RuCl_2$-[(R)-binap][(R,R)-dpen] (0.21 mg, 0.0021 mmol), 3-quinuclidinone (0.526 g, 4.2 mmol), $KOC(CH_3)_3$ (9.4 mg, 0.084 mmol) were placed in a 100-mL glass autoclave, replaced with argon, subsequently added with 2-propanol (10 mL), degassed and replaced with argon. Hydrogen was introduced until the pressure became 10 atm at 30° C., and the reaction was started. After the reaction solution was stirred for 14 h, the reaction pressure was decreased to a normal pressure, and the quantity and optical purity of the product 3-quinuclidinol were determined by gas chromatography of the reaction solution; the result showed that (R)-3-quinuclidinol with 40% ee was formed with a yield of 5%.

Comparative Example 3

$RuCl_2$-[(R)-binap][(R,R)-dpen] (0.21 mg, 0.0021 mmol), 3-quinuclidinone (0.526 g, 4.2 mmol), $KOC(CH_3)_3$ (9.4 mg, 0.084 mmol) were placed in a 100-mL glass autoclave, replaced with argon, subsequently added with 2-propanol (10 mL) and $B(Oi-Pr)_3$ (0.0079 g, 0.042 mmol), degassed and replaced with argon. Hydrogen was introduced until the pressure became 10 atm at 30° C., and the reaction was started. After the reaction solution was stirred for 14 h, the reaction pressure was decreased to a normal pressure, and the quantity and optical purity of the product 3-quinuclidinol were determined by gas chromatography of the reaction solution; the result showed that (R)-3-quinuclidinol with 47% ee was formed with a yield of 36%.

TABLE 2

| | Ru complex | Substrate/ Ru complex/base | $H_2$ (atm) | Solvent | Temperature (° C.) | Time (h) | Yield (%) | ee(%) |
|---|---|---|---|---|---|---|---|---|
| Example 25 | (R,R)-XylSKEWPHOS (S)-AMP | 1000/1/40 | 10 | EtOH | 30 | 19 | 96 | 86 (s) |
| Example 26 | (R,R)-XylSKEWPHOS (S)-AMP | 1000/1/40 | 10 | 2-propanol | 30 | 19 | 99 | 66 (S) |
| Example 27 | (R,R)-XylSKEWPHOS (S)-AMP | 1000/1/40 | 10 | EtOH:BuOH = 3:1 | 30 | 19 | 95 | 86 (S) |
| Example 28 | (R,R)-XylSKEWPHOS (S)-AMP | 500/1/40 | 10 | EtOH | 0 | 19 | 89 | 88 (S) |
| Example 29 | (S,S)-XylSKEWPHOS (R)-AMEP | 1000/1/40 | 10 | EtOH | 30 | 19 | 89 | 65 (R) |

Diphosphine ligand

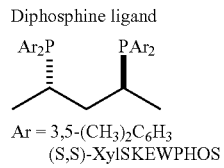

Ar = 3,5-$(CH_3)_2C_6H_3$
(S,S)-XylSKEWPHOS

Amin ligand

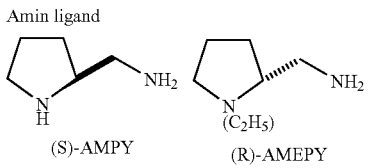

(S)-AMPY    (R)-AMEPY

Comparative Example 4

RuCl$_2$-[(S)-binap][(R,R)-dpen] (0.2 mg, 0.002 mmol) synthesized by the method described in JP (A) No. 11-289600, 3-quinuclidinone (0.250 g, 2 mmol), KOC(CH$_3$)$_3$ (9 mg, 0.08 mmol) were placed in a 100-mL glass autoclave, replaced with argon, subsequently added with 2-propanol (4 mL)), degassed and replaced with argon. Hydrogen was introduced until the pressure became 10 atm at 30° C., and the reaction was started. After the reaction solution was stirred for 19 h, the reaction pressure was decreased to a normal pressure, and the quantity and optical purity of the product 3-quinuclidinol were determined by gas chromatography of the reaction solution; the result showed that (R)-3-quinuclidinol with 9% ee was formed with a yield of 52%.

Comparative Example 5

Hydrogenation of 3-quinuclidinone was carried out similar to the Example 25, except that RuCl$_2$-[(S)-tolbinap][(S)-ampy] synthesized by the method described in the Example 19 was used as the catalyst in place of RuBr$_2$-[(R,R)-xylskewphos] [(S)-ampy], and (S)-3-quinuclidinol with 32% ee was formed with a yield of 3%.

Comparative Example 6

Hydrogenation of 3-quinuclidinone was carried out similar to the Example 9, except that RuCl$_2$-[(S,S)-meduphos](pica) synthesized by the method described in the Example 19 was used as the catalyst in place of RuBr$_2$-[(S,S)-xylskewphos](pica), and (R)-3-quinuclidinol with 14% ee was formed with a yield of 95%.

Comparative Example 7

Hydrogenation of 3-quinuclidinone was carried out similar to the Example 9, except that RuCl$_2$-[(S,S)-norphos](pica) synthesized by the method described in the Example 19 was used as the catalyst in place of RuBr$_2$-[(S,S)-xylskewphos](pica), and (R)-3-quinuclidinol with 12% ee was formed with a yield of 94%.

Comparative Example 8

Hydrogenation of 3-quinuclidinone was carried out similar to the Example 9, except that RuCl$_2$-[(S,S)-chiraphos](pica) synthesized by the method described in the Example 1 was used as the catalyst in place of RuBr$_2$-[(S,S)-xylskewphos](pica), and (R)-3-quinuclidinol with 24% ee was formed with a yield of 89%.

Comparative Example 9

Hydrogenation of 3-quinuclidinone was carried out similar to the Example 25, except that RuCl$_2$-[(S,S)-chiraphos] [(S)-ampy] synthesized by the method described in the Example 19 was used as the catalyst in place of RuBr$_2$-[(R,R)-xylskewphos] [(S)-ampy], and (R)-3-quinuclidinol with 7% ee was formed with a yield of 91%.

TABLE 3

| | Ru complex | Substrate/ Ru complex/base | Additive | H$_2$ (atm) | Solvent | Temperature (° C.) | Time (h) | Yield (%) | ee (%) |
|---|---|---|---|---|---|---|---|---|---|
| Comparative Example 1 | (S,S)-XylSKEWPHOS (S)-DAIPEN | 1000/1/40 | — | 10 | EtOH | 30 | 19 | 50 | 38 (S) |
| Comparative Example 2 | (R)-BINAP (R,R)-DPEN | 2000/1/40 | — | 10 | 2-propanol | 30 | 14 | 5 | 40 (R) |
| Comparative Example 3 | (R)-BINAP (R,R)-DPEN | 2000/1/40 | B(OI-Pr)$_3$:Ru = 20:1 | 10 | 2-propanol | 30 | 14 | 36 | 47 (R) |
| Comparative Example 4 | (S)-BINAP (R,R)-DPEN | 1000/1/40 | — | 10 | 2-propanol | 30 | 19 | 52 | 9 (R) |
| Comparative Example 5 | (S)-TolBINAP (S)-AMPY | 1000/1/40 | — | 10 | EtOH | 30 | 19 | 3 | 32 (S) |
| Comparative Example 6 | (S,S)-MeDUPHOS PICA | 1000/1/40 | — | 10 | EtOH | 30 | 19 | 95 | 14 (R) |
| Comparative Example 7 | (S,S)-NORPHOS PICA | 1000/1/40 | — | 10 | EtOH | 30 | 19 | 94 | 12 (R) |
| Comparative Example 8 | (S,S)-CHIRAPHOS PICA | 1000/1/40 | — | 10 | EtOH | 30 | 19 | 89 | 24 (R) |
| Comparative Example 9 | (S,S)-CHIRAPHOS (S)-AMPY | 1000/1/40 | — | 10 | EtOH | 30 | 19 | 91 | 7 (R) |

Diphosphine ligand

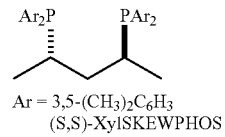

Ar = 3,5-(CH$_3$)$_2$C$_6$H$_3$
(S,S)-XylSKEWPHOS

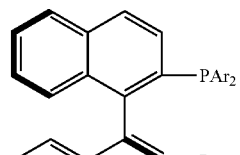

Ar = C$_6$H$_5$ (S)-BINAP
4-(CH$_3$)C$_6$H$_4$ (S)-TolBINAP

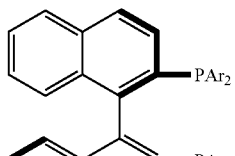

Ar = C$_6$H$_5$ (R)-BINAP

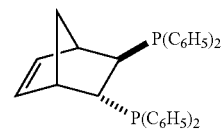

(S,S)-NORPHOS

TABLE 3-continued

| | Substrate/ | | H₂ | | Temperature | Time | Yield | |
|---|---|---|---|---|---|---|---|---|
| Ru complex | Ru complex/base | Additive | (atm) | Solvent | (° C.) | (h) | (%) | ee (%) |

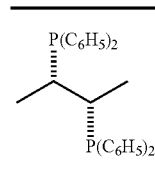
(S,S)-CHIRAPHOS

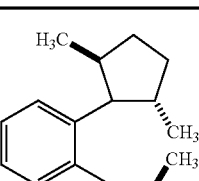
(S,S)-MeDUPHOS

Amin ligand

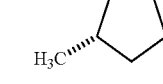
(R)-DAIPEN

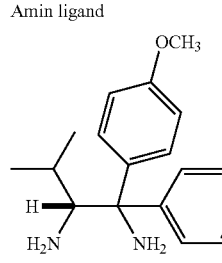
(S)-DAIPEN

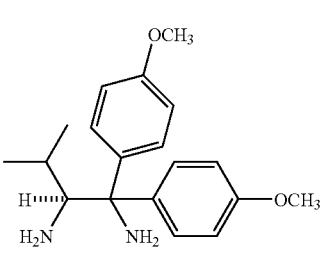
(R,R)-DPEN

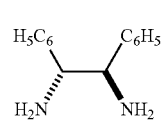
PICA

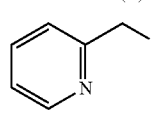
(S)-AMPY

Example 30

RuCl₂-[(S,S)-xylskewphos](dmf)n (0.002 mmol) prepared from (S,S)-XylSKEWPHOS and [RuCl₂(p-cymene)]₂, 2-picolylamine (0.2 mg, 0.002 mmol), 3-quinuclidinone (0.250 g, 2 mmol), and KOC(CH₃)₃ (9 mg, 0.08 mmol) were placed in a 100-mL glass autoclave, replaced with argon, subsequently added with ethanol (4 mL), degassed and replaced with argon. Hydrogen was introduced until the pressure became 10 atm at 30° C., and the reaction was started. After the reaction solution was stirred for 19 h, the reaction pressure was decreased to a normal pressure, and the quantity and optical purity of the product 3-quinuclidinol were determined by gas chromatography of the reaction solution; the result showed that (R)-3-quinuclidinol with 90% ee was formed with a yield of 100%.

Industrial Applicability

The above novel ruthenium complexes according to the invention are superior than conventional ruthenium complex catalysts having an optically active diphosphine compound with axial asymmetry or asymmetry on carbon and an optically active 1,2-diethylenediamine-type diamine compound as the ligands, in terms of reactivity, enantioselectivity and others in the asymmetric hydrogenation of 3-quinuclidinols, and they have excellent industrial usefulness.

The invention cliamed is:
1. A ruthenium complex of general formula (1):

$$RuXYAB \quad (1)$$

wherein X and Y may be mutually identical or different and denote hydrogen or an anion group, A is a compound of general formula (2):

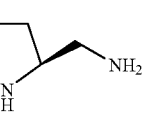

wherein $R^1$ and $R^2$ may be mutually identical or different and are an alkyl group having a carbon number of 1-20 or a cyclic hydrocarbon group which may have one or more substituents; $R^3$ and $R^4$ may be mutually identical or different and are hydrogen or a hydrocarbon group having a carbon number of 1-3; $R^5$, $R^6$, $R^7$ and $R^8$ may be mutually identical or different and are a phenyl group substituted with 1 to 5 methyl, ethyl, propyl, or t-butyl groups, B is a compound of general formula (3) or (4):

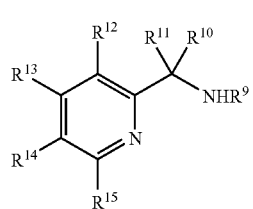

-continued

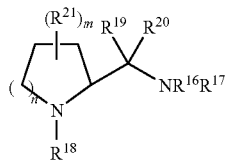
(4)

wherein in general formula (3), $R^9$ denotes a hydrogen atom, an alkyl group having a carbon number of 1-20 or a cyclic hydrocarbon group which may have one or more substituents; $R^{10}$ and $R^{11}$ may be mutually identical or different and denote a hydrogen atom, an alkyl group having a carbon number of 1-20 or a cyclic hydrocarbon group which may have one or more substituents, $R^{10}$ and $R^{11}$ may be mutually bonded to form a saturated or unsaturated hydrocarbon group which may have one or more substituents of alkyl, alkenyl, cycloalkyl, aryl, alkoxy, ester, acyloxy, halogen atoms, nitro, or cyano; $R^{12}$, $R^{13}$, $R^{14}$ and $R^{15}$ may be mutually identical or different and denote a hydrogen atom, an alkyl group having a carbon number of 1-20 or a cyclic hydrocarbon group which may have one or more substituents, $R^{12}$ and $R^{13}$, $R^{13}$ and $R^{14}$, or $R^{14}$ and $R^{15}$ may be mutually bonded to form a saturated or unsaturated hydrocarbon group, or to form a saturated or unsaturated hydrocarbon group containing N; wherein in general formula (4), at least one of $R^{16}$, $R^{17}$ and $R^{18}$ is a hydrogen atom, $R^{16}$ and $R^{17}$ may be mutually identical or different and denote a hydrogen atom, an alkyl group having a carbon number of 1-20 or a cyclic hydrocarbon group which may have one or more substituents, or $R^{16}$ and $R^{17}$ may be mutually bonded to form a ring containing N, $R^{18}$ denotes a hydrogen atom, an alkyl group having a carbon number of 1-20 or a cyclic hydrocarbon group which may have one or more substituents; $R^{19}$ and $R^{20}$ may be mutually identical or different and denote a hydrogen atom, an alkyl group having a carbon number of 1-20 or a cyclic hydrocarbon group which may have one or more substituents, $R^{19}$ and $R^{20}$ may be mutually bonded to form a saturated or unsaturated hydrocarbon group which may have one or more substituents of alkyl, alkenyl, cycloalkyl, aryl, alkoxy, ester, acyloxy, halogen atoms, nitro, or cyano;

$R^{21}$ may be mutually identical or different and independently denote a hydrogen atom, an alkyl group having a carbon number of 1-20 or a cyclic hydrocarbon group which may have one or more substituents, and adjacent $R^{21}$ may be mutually bonded to form a saturated or unsaturated hydrocarbon group; m denotes an integer of 1-10; n denotes an integer of 1-3, and wherein each ligand of the ruthenium may be arbitrarily coordinated.

2. The ruthenium complex according to claim 1, wherein

A is one selected from the group consisting of TolSKEWPHOS:2,4-bis(di-4-tolylphosphino)pentane, XylSKEWPHOS:2,4-bis(di-3,5-xylylphosphino)pentane, 4-t-BuSKEWPHOS:2,4-bis[di(4-t-butylphenyl)phosphino]pentane, 3,5-diEtSKEWPHOS:2,4-bis[bis(3,5-diethylphenyl)phosphino]pentane, 2,4-bis(diphenylphosphino)-3-methylpentane, 2,4-bis(di-4-tolylphosphino)-3-methylpentane, 2,4-bis(di-3,5-xylylphosphino)-3-methylpentane, 2,4-bis[di(4-t-butylphenyl)phosphino]-3-methylpentane, 2,4-bis[bis(3,5-diethylphenyl)phosphino]-3-methylpentane, 1,3-bis(diphenylphosphino)-1,3-diphenylpropane, 1,3-bis(di-4-tolylphosphino)-1,3-diphenylpropane, 1,3-bis(di-3,5-xylylphosphino)-1,3-diphenylpropane, 1,3-bis[di(4-t-butylphenyl)phosphino]-1,3-diphenylpropane, 1,3-bis[bis(3,5-diethylphenyl)phosphino]-1,3-diphenylpropane, 1,3-bis(diphenylphosphino)-1,3-diphenyl-2-methylpropane, 1,3-bis(di-4-tolylphosphino)-1,3-diphenyl-2-methylpropane, 1,3-bis(di-3,5-xylylphosphino)-1,3-diphenyl-2-methylpropane, 1,3-bis[di(4-t-butylphenyl)phosphino]-1,3-diphenyl-2-methylpropane, and 1,3-bis[bis(3,5-diethylphenyl)phosphino]-1,3-diphenyl-2-methylpropane, B is one represented by general formula (3), wherein $R^9$ denotes a hydrogen atom, an alkyl group having a carbon number of 1-10 or a cyclic hydrocarbon group which may have one or more substituents; $R^{10}$ and $R^{11}$ may be mutually identical or different and denote a hydrogen atom, an alkyl group having a carbon number of 1-10 or a cyclic hydrocarbon group which may have one or more substituents, $R^{10}$ and $R^{11}$ may be mutually bonded to form a saturated or unsaturated hydrocarbon group which may have one or more substituents of alkyl, alkenyl, cycloalkyl, aryl, alkoxy, ester, acyloxy, halogen atoms, nitro, or cyano; $R^{12}$, $R^{13}$, $R^{14}$ and $R^{15}$ may be mutually identical or different and denote a hydrogen atom, an alkyl group having a carbon number of 1-10 or a cyclic hydrocarbon group which may have one or more substituents, $R^{12}$ and $R^{13}$, $R^{13}$ and $R^{14}$, or $R^{14}$ and $R^{15}$ may be mutually bonded to form a saturated or unsaturated hydrocarbon group; or by general formula (4), wherein at least one of $R^{16}$, $R^{17}$ and $R^{18}$ is a hydrogen atom, $R^{16}$ and $R^{17}$ may be mutually identical or different and denote a hydrogen atom, an alkyl group having a carbon number of 1-10 or a cyclic hydrocarbon group which may have one or more substituents, or $R^{16}$ and $R^{17}$ may be mutually bonded to form a ring containing N, $R^{18}$ denotes a hydrogen atom, an alkyl group having a carbon number of 1-10 or a cyclic hydrocarbon group which may have one or more substituents; $R^{19}$ and $R^{20}$ may be mutually identical or different and denote a hydrogen atom, an alkyl group having a carbon number of 1-10 or a cyclic hydrocarbon group which may have one or more substituents, $R^{19}$ and $R^{20}$ may be mutually bonded to form a saturated or unsaturated hydrocarbon group which may have one or more substituents of alkyl, alkenyl, cycloalkyl, aryl, alkoxy, ester, acyloxy, halogen atoms, nitro, or cyano; $R^{21}$ may be mutually identical or different and independently denote a hydrogen atom, an alkyl group having a carbon number of 1-10 or a cyclic hydrocarbon group which may have one or more substituents, and adjacent $R^{21}$ may be mutually bonded to form a saturated or unsaturated hydrocarbon group;

m denotes an integer of 1-10, n denotes an integer of 1-3, and the ruthenium may be arbitrarily coordinated with each ligand.

3. The ruthenium complex according to claim 1, wherein

A is one selected from the group consisting of TolSKEWPHOS:2,4-bis(di-4-tolylphosphino)pentane, XylSKEWPHOS:2,4-bis(di-3,5 -xylylphosphino)pentane, 4-t-BuSKEWPHOS:2,4-bis[di(4-t-butylphenyl)phosphino]pentane, and 3,5 -diEtSKEWPHOS:2,4-bis[bis(3,5 -diethylphenyl)phosphino]pentane, B is 2-picolylamine or 2-aminomethylpyrrolidine.

4. A process for preparing the compound of general formula (1) according to claim 1,

wherein a compound of general formula (5):

is reacted with the compound B to obtain said compound of general formula (1), wherein X, Y, A, and B are as defined in claim 1.

5. A process for preparing optically active 3-quinuclidinols, wherein 3-quinuclidinones are reacted with hydrogen or a hydrogen-donating compound in the presence of a ruthenium complex of general formula (1):

wherein X and Y may be mutually identical or different and denote hydrogen or an anion group,
A is a compound of general formula (2):

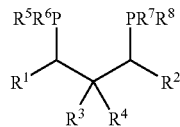

wherein $R^1$ and $R^2$ may be mutually identical or different and are an alkyl group having a carbon number of 1-20 or a cyclic hydrocarbon group which may have one or more substituents; $R^3$ and $R^4$ may be mutually identical or different and are hydrogen or a hydrocarbon group having a carbon number of 1-3; $R^5$, $R^6$, $R^7$ and $R^8$ may be mutually identical or different and are a hydrocarbon group which may have one or more substituents,
B is a compound of general formula (3) or (4):

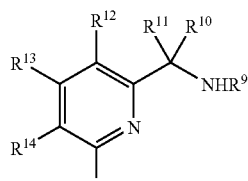

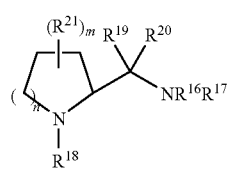

wherein in general formula (3), $R^9$ denotes a hydrogen atom, an alkyl group having a carbon number of 1-20 or a cyclic hydrocarbon group which may have one or more substituents; $R^{10}$ and $R^{11}$ may be mutually identical or different and denote a hydrogen atom, an alkyl group having a carbon number of 1-20 or a cyclic hydrocarbon group which may have one or more substituents, $R^{10}$ and $R^{11}$ may be mutually bonded to form a saturated or unsaturated hydrocarbon group which may have one or more substituents of alkyl, alkenyl, cycloalkyl, aryl, alkoxy, ester, acyloxy, halogen atoms, nitro, or cyano; $R^{12}$, $R^{13}$, $R^{14}$ and $R^{15}$ may be mutually identical or different and denote a hydrogen atom, an alkyl group having a carbon number of 1-20 or a cyclic hydrocarbon group which may have one or more substituents, $R^{12}$ and $R^{13}$, $R^{13}$ and $R^{14}$, or $R^{14}$ and $R^{15}$ may be mutually bonded to form a saturated or unsaturated hydrocarbon group, or to form a saturated or unsaturated hydrocarbon group containing N; wherein in general formula (4), at least one of $R^{16}$, $R^{17}$ and $R^{18}$ is a hydrogen atom, $R^{16}$ and $R^{17}$ may be mutually identical or different and denote a hydrogen atom, an alkyl group having a carbon number of 1-20 or a cyclic hydrocarbon group which may have one or more substituents, or $R^{16}$ and $R^{17}$ may be mutually bonded to form a ring containing N, $R^{18}$ denotes a hydrogen atom, an alkyl group having a carbon number of 1-20 or a cyclic hydrocarbon group which may have one or more substituents; $R^{19}$ and $R^{20}$ may be mutually identical or different and denote a hydrogen atom, an alkyl group having a carbon number of 1-20 or a cyclic hydrocarbon group which may have one or more substituents, $R^{19}$ and $R^{20}$ may be mutually bonded to form a saturated or unsaturated hydrocarbon group which may have one or more substituents of alkyl, alkenyl, cycloalkyl, aryl, alkoxy, ester, acyloxy, halogen atoms, nitro, or cyano;
$R^{21}$ may be mutually identical or different and independently denote a hydrogen atom, an alkyl group having a carbon number of 1-20 or a cyclic hydrocarbon group which may have one or more substituents, and adjacent $R^{21}$ may be mutually bonded to form a saturated or unsaturated hydrocarbon group; m denotes an integer of 1-10; n denotes an integer of 1-3, or a ruthenium complex of general formula (5):

wherein X and Y may be mutually identical or different and denote hydrogen or an anion group, identical or different and denote hydrogen or an anion group, and
A is a compound of general formula (2):

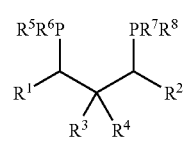

wherein $R^1$ and $R^2$ may be mutually identical or different and are an alkyl group having a carbon number of 1-20 or a cyclic hydrocarbon group which may have one or more substituents; $R^3$ and $R^4$ may be mutually identical or different and are hydrogen or a hydrocarbon group having a carbon number of 1-3; $R^5$, $R^6$, $R^7$ and $R^8$ may be mutually identical or different and are a hydrocarbon group which may have one or more substituents, and a diamine compound or an optically active diamine compound of general formula (3) or (4):

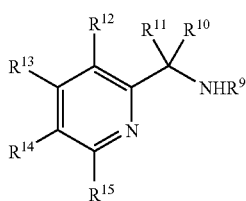

(3)

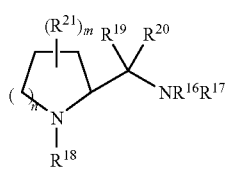

(4)

wherein $R^9$ denotes a hydrogen atom, an alkyl group having a carbon number of 1-20 or a cyclic hydrocarbon group which may have one or more substituents; $R^{10}$ and $R^{11}$ may be mutually identical or different and denote a hydrogen atom, an alkyl group having a carbon number of 1-20 or a cyclic hydrocarbon group which may have one or more substituents, $R^{10}$ and $R^{11}$ may be mutually bonded to form a saturated or unsaturated hydrocarbon group which may have one or more substituents of alkyl, alkenyl, cycloalkyl, aryl, alkoxy, ester, acyloxy, halogen atoms, nitro, or cyano; $R^{12}$, $R^{13}$, $R^{14}$ and $R^{15}$ may be mutually identical or different and denote a hydrogen atom, an alkyl group having a carbon number of 1-20 or a cyclic hydrocarbon group which may have one or more substituents, $R^{12}$ and $R^{13}$, $R^{13}$ and $R^{14}$, or $R^{14}$ and $R^{15}$ may be mutually bonded to form a saturated or unsaturated hydrocarbon group, or to form a saturated or unsaturated hydrocarbon group containing N; wherein in general formula (4), at least one of $R^{16}$, $R^7$ and $R^{18}$ is a hydrogen atom, $R^{16}$ and $R^{17}$ may be mutually identical or different and denote a hydrogen atom, an alkyl group having a carbon number of 1-20 or a cyclic hydrocarbon group which may have one or more substituents, or $R^{16}$ and $R^{17}$ may be mutually bonded to form a ring containing N, $R^{18}$ denotes a hydrogen atom, an alkyl group having a carbon number of 1-20 or a cyclic hydrocarbon group which may have one or more substituents; $R^{19}$ and 20 may be mutually identical or different and denote a hydrogen atom, an alkyl group having a carbon number of 1-20 or a cyclic hydrocarbon group which may have one or more substituents, $R^{19}$ and $R^{20}$ may be mutually bonded to form a saturated or unsaturated hydrocarbon group which may have one or more substituents of alkyl, alkenyl, cycloalkyl, aryl, alkoxy, ester, acyloxy, halogen atoms, nitro, or cyano; $R^{21}$ may be mutually identical or different and independently denote a hydrogen atom, an alkyl group having a carbon number of 1-20 or a cyclic hydrocarbon group which may have one or more substituents, and adjacent $R^{21}$ may be mutually bonded to form a saturated or unsaturated hydrocarbon group; m denotes an integer of 1-10; n denotes an integer of 1-3;

to obtain the optically active 3-quinuclidinols.

6. A process for preparing optically active 3-quinuclidinols according to claim 5, wherein 3-quinuclidinones are reacted with hydrogen or a hydrogen-donating compound in the presence of a ruthenium complex of general formula (1):

RuXYAB  (1)

wherein X is hydrogen, Y is a tetrahydroborate anion or a tetrafluoroborate anion, A and B are as defined in claim 5, to obtain the optically active 3-quinuclidinols.

7. A process for preparing optically active 3-quinuclidinols according to claim 5, wherein 3-quinuclidinones are reacted with hydrogen or a hydrogen-donating compound in the presence of a ruthenium complex of general formula (1):

RuXYAB  (1)

wherein X, Y, A and B are as defined in claim 5, and a base represented by an alkali metal or alkaline earth metal salt, or a quaternary ammonium salt, to obtain the optically active 3-quinuclidinols.

8. A process for preparing optically active 3-quinuclidinols according to claim 5, wherein 3-quinuclidinones are reacted with hydrogen or a hydrogen-donating compound in the presence of a ruthenium complex of general formula (5):

RuXYA  (5)

wherein X is hydrogen, Y is a tetrahydroborate anion or a tetrafluoroborate anion, and A is as defined in claim 5, and a diamine compound or an optically active diamine compound of general formula (3) or (4):

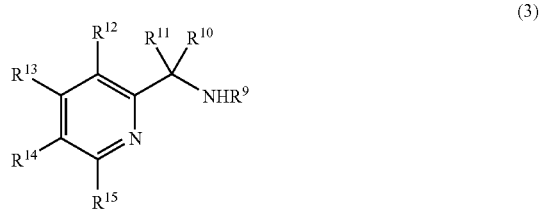

(3)

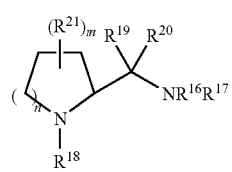

(4)

wherein $R^9$-$R^{21}$, n and m are as defined in claim 5, to obtain the optically active 3-quinuclidinols.

9. A process for preparing optically active 3-quinuclidinols according to claim 5, wherein 3-quinuclidinones are reacted with hydrogen or a hydrogen-donating compound in the presence of a ruthenium complex of general formula (5):

RuXYA    (5)

wherein X, Y and A are as defined in claim 5, a diamine compound or an optically active diamine compound of general formula (3) or (4):

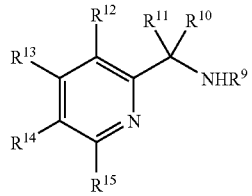 (3)

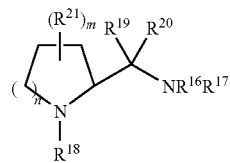 (4)

wherein $R^9$-$R^{21}$, n and m are as defined in claim 5, and a base such as an alkali metal or alkaline earth metal salt, or a quaternary ammonium salt, to obtain the optically active 3-quinuclidinols.

* * * * *